(12) United States Patent
Da Silva et al.

(10) Patent No.: US 8,263,947 B2
(45) Date of Patent: Sep. 11, 2012

(54) METHOD AND DEVICE FOR LOCALISING FLUOROPHORES OR ABSORBERS IN A SURROUNDING MEDIUM

(75) Inventors: Anabela Da Silva, Marseilles (FR); Jean-Marc Dinten, Lyons (FR); Philippe Rizo, La Tronche (FR)

(73) Assignee: Commissariat a l'Energie Atomique, Paris (FR)

( * ) Notice: Subject to any disclaimer, the term of this patent is extended or adjusted under 35 U.S.C. 154(b) by 298 days.

(21) Appl. No.: 12/616,502

(22) Filed: Nov. 11, 2009

(65) Prior Publication Data

US 2010/0155622 A1 Jun. 24, 2010

(30) Foreign Application Priority Data

Nov. 13, 2008 (FR) ..................................... 08 57699

(51) Int. Cl.
*G01J 1/58* (2006.01)
(52) U.S. Cl. .................................................. 250/459.1
(58) Field of Classification Search ................ 250/459.1
See application file for complete search history.

(56) References Cited

U.S. PATENT DOCUMENTS

| | | | |
|---|---|---|---|
| 6,058,324 A | 5/2000 | Chance | |
| 7,010,341 B2 * | 3/2006 | Chance | 600/476 |
| 7,675,044 B2 | 3/2010 | Laidevant et al. | |
| 2008/0067420 A1 | 3/2008 | Laidevant et al. | |

FOREIGN PATENT DOCUMENTS

WO WO 2006/032151 A1 3/2006

OTHER PUBLICATIONS

Laurent Guyon et al., "Time-Resolved Fluorescence Tomography in Cancer Research: Backward Versus Toward Geometry", Proceedings of SPIE, 2009, CEA, LETI, Departement Microtechnologies pour la Biologie et la Sante, XP-002579495, 6 Pages.

Huiyan HE et al., "An Analytic, Reflection Method for Time-Domain Florescence Diffuse Optical Tomography Based on a Generalized Pulse Spectrum Technique", Progress in Biomedical Optics and Imaging, Proceedings of SPIE, 2008, College of Precision Instruments and Optoelectronics Engineering, Tianjin University, XP-002579460, 5 Pages.

(Continued)

*Primary Examiner* — David Porta
*Assistant Examiner* — Hugh H Maupin
(74) *Attorney, Agent, or Firm* — Oblon, Spivak, McClelland, Maier & Neustadt, L.L.P.

(57) ABSTRACT

The invention relates to a method of localising a fluorophore (22) in a scattering medium (20), by means of a radiation source (8, 10) suited to emitting an excitation radiation of this fluorophore and detection means (4, 12) suited to measuring a fluorescence signal ($\Phi_{fluo}$) emitted by this fluorophore (22) comprising:

a) for at least 3 different pairs of positions of the radiation source and detection means, an excitation by a radiation coming from the radiation source (8), and a detection by means (4) of detecting the fluorescence signal emitted by this fluorophore after this excitation, b) for each of these pairs, the identification of a surface on which the fluorophore is situated, or a volume comprising this surface and in which the fluorophore is situated, c) an estimation of the localisation of the fluorophore in its surrounding medium, by calculation of the intersection of the three surfaces, or if necessary a volume around this intersection.

28 Claims, 15 Drawing Sheets

OTHER PUBLICATIONS

Aurelie Laidevant et al., "Effects of the Surface Boundary on the Determination of the Optical Properties of a Turbid Medium with Time-Resolved Reflectance", Applied Optics, vol. 45, No. 19, Jul. 1, 2006, pp. 4756-4764.

Aurelie Laidevant, "Methodes Optiques Resolues en Temps pour la Tomographie de Fluorescence dans les Milieux Diffusants", Oct. 5, 2006, Laboratoire Imagerie et Systemes d'Acquistion—Cea-Leti Grenoble, XP-002532320, 187 Pages.

Michael S. Patterson et al., "Time Resolved Reflectance and Transmittance for the Non-Invasive Measurement of Tissue Optical Properties", Applied Optics, vol. 28, No. 12, Jun. 15, 1989, pp. 2331-2336.

Jun Wu et al., "Fluorescence Tomographic Imaging in Turbid Media Using Early-Arriving Photons and Laplace Transforms", Proceedings of the National Academy of Sciences, vol. 94, Aug. 1997, pp. 8783-8788.

\* cited by examiner

METHOD AND DEVICE FOR LOCALISING FLUOROPHORES OR ABSORBERS IN A SURROUNDING MEDIUM

TECHNICAL FIELD AND PRIOR ART

The invention relates to the field of diffuse optical imaging on biological tissues by time resolved methods.

It applies to the localisation of fluorophores or absorbers in a scattering medium such as, for example, an organ of an animal or a human being (brain, breast, any organ where fluorophores may be injected).

In particular, an interest of a molecule that absorbs is as follows. Certain cancerous tumours are visible by the simple fact that they have a higher attenuation coefficient than healthy tissues. In this case, it is important to be able to identify these tumours.

In this context, use may also be made of a fluorophore, which is a specific fluorescent label. This fixes in a preferential manner onto target cells of interest (for example cancerous cells). Such a fluorophore offers a better detection contrast than a non specific label. The aim of fluorescence molecular imaging optical techniques is to localise spatially these fluorescent labels.

Optical tomography systems use various light sources. Devices thus exist that operate in continuous mode, others in frequency mode (which use frequency modulated lasers) and finally devices operating in time mode, which use pulsed lasers.

Thus, three diffuse optical imaging methods exist, which differ from each other depending on whether the light source used is continuous, in frequency mode (i.e. the intensity of which is modulated by a sinusoidal function of time) or pulsed.

Instruments using a continuous light source were the first to be used, the light source being a filtered white source or a monochromatic source, such as a laser. Spot or two-dimensional detectors measuring the intensity of the light reflected or transmitted by a tissue illuminated by the light source were then used.

The second category of diffuse optical imaging, known as frequency imaging, uses a light source intensity modulated at a given frequency. The light source is usually a laser source intensity modulated at frequencies f generally between several tens of kHz to several hundreds of MHz. The detector used measures both the amplitude of the light signal reflected or transmitted by the tissue, as well as the phase of this light signal compared to that of the light source.

Finally, the third category of diffuse optical imaging is pulsed diffuse optical imaging, also known as pulsated, or instead temporal, or instead time resolved diffuse optical imaging. The source used produces light pulses known as pulsated light, in other words of short duration, at a given repetition rate.

The sources used may be picosecond pulsed laser diodes, or femtosecond lasers. Since the duration of the pulse is generally less than 1 ns, the expression sub-nanosecond pulsed light sources is then used. The repetition rate is usually between several hundreds of kHz to several hundreds of MHz.

The invention relates to this third fluorescence imaging category.

Temporal data is data that contains the most informational content on the tissue traversed, but for which the reconstruction techniques are the most complex. The measure at each acquisition point is in fact a time dependent function known as TPSF for Temporal Point Spread Function).

The aim is to extract simple parameters of the TPSF, the theoretical expression of which is moreover known. Then, the resolution of the inverse problem enables the distribution of the fluorescent labels to be found.

In certain cases, the aim is to localise a fluorophore for the purpose of a subsequent intervention. At the present time, the localisation of diseased cells may be carried out by means of biopsy techniques. But, in order to find the position, even approximate, of these cells, several samples have to be taken. This invasive technique is obviously difficult to implement and time consuming.

The problem is thus posed of determining the localisation, even in an approximate manner, of a fluorophore or an absorber fixed on a zone of a medium, for example a biological medium, and to do so with a limited number of measures, and a relatively short breakdown time, even close to real time. The invention finds its full usefulness for carrying out such a determination in media having a limited accessibility, for example during the screening of cancerous tumours of the prostate from endoscopic measures, or during the screening of breast cancers, or osteosarcoma cancers, etc.

DESCRIPTION OF THE INVENTION

The invention firstly relates to a method of localising at least one fluorophore or at least one absorbent element (particularly molecule)—also known as absorber—in a scattering medium, by means of a radiation source suited to emitting an excitation radiation of this fluorophore and detection means suited to measuring:

a fluorescence signal ($\Phi_{fluo}$) emitted by this fluorophore, or a signal re-emitted at the same wavelength as that of excitation (stemming from the radiation source) by the absorbent element that absorbs and diffuses the absorbed radiation. The absorbent element may form part of a zone of a medium that has an absorption coefficient higher than that of the scattering medium. The example of certain cancerous tumours has already been given.

This localisation method comprises the following steps:

a) for at least 3 different pairs of positions of the radiation source and detection means, at least one excitation by a radiation coming from the radiation source, and at least one detection by the detection means of the fluorescence signal emitted by this fluorophore after this excitation, or of the emission signal emitted by the absorber or by the absorbent element, b) for each of these pairs, the identification of a surface on which the fluorophore (or the absorbent element) is situated, or of a volume comprising this surface and in which the fluorophore or the absorber is situated, c) an estimation of the localisation of the fluorophore or the localisation of the absorbent element in its scattering medium, by calculation of the intersection of three surfaces, or if necessary in a volume around this intersection.

Such a method may be implemented whatever the respective positions of the fluorophore or the absorber, the source and detector.

The precision of the method will not be the same depending on whether positions of the source and the detection means are taken close to or far from the fluorophore or the absorber. But the method enables in all cases a localisation, even crude, with a low number of measures, with a rapid breakdown, or even in real time. Such a method thus makes it possible to direct the carrying out of additional non-invasive biopsies or examinations.

Furthermore, this method may be implemented very rapidly, a localisation of a fluorophore or absorber may be carried out in less than one minute, or even in less than 15 s.

For each pair of at least 3 different pairs, a histogram may be defined representing the number of photons detected as a function of time; this histogram may be called fluorescence time function.

The radiation or light source and the detection means may be respectively the end of an optic fibre that brings the excitation light into the medium and the end of an optic fibre that receives a part of the emission light. For the source, it may also be a laser or LED type light source. As regards the detector, it may be a photomultiplier tube, or an image sensor.

According to the invention, the element targeted by the detection may be a single fluorophore, or a plurality or an aggregation of fluorophores grouped substantially in a same place. It may also be an absorber or a plurality of absorbers grouped substantially in a same place (aggregation). In the remainder of the text, an absorber will be assimilated with a fluorophore, the emission wavelength of which is equal to the excitation wavelength and the lifetime of which is zero. In other words an absorbent medium, or an absorber, is a fluorophore, the emission wavelength of which is equal to the excitation wavelength, and the time constant $\tau$ of which is zero. The expression "fluorophore" will thus only be used, except unless the specificities of the absorbers are explained.

The volume around the intersection of the three calculated surfaces may result from the intersection of three volumes, each volume being associated with one of the surfaces and comprising all of the points of the surface and all of the points that satisfy the equation of the surface with an error margin, for example ±10% or ±5%.

The scattering medium surrounding the fluorophore may have any geometric shape: for example, it is of infinite type.

It may also be of semi-infinite type, limited by a wall. A semi-infinite medium, for which each of the ends of fibres for bringing the excitation signal and receiving the fluorescence signal is laid out at more than 1 cm, or 1.5 cm or 2 cm from the wall that limits this medium may be considered, from the point of view of the method according to the invention, as an infinite medium.

The scattering medium may also form a slab (geometry known as "slab" geometry), limited by two parallel surfaces. The invention also applies to a medium of any shape, the exterior surface of which is broken down into a series of planes.

In certain embodiments, the surfaces at the intersection of which the fluorophore is found may have the shape of ellipsoids, but 3D surfaces not having this shape are also possible.

According to one embodiment, step b) comprises for each position pair, a calculation of a normalised time moment, of order n (n≧1), of a fluorescence time function. Such a moment may be obtained by an $n^{th}$ order derivative of a transform of said fluorescence time function, for example a Fourier transform, or a Laplace transform or a Mellin transform.

It will be recalled that a normalised moment of order n (n≧1), noted $m_n$, of a distribution g(t) is defined by $$m_n = \frac{\int_{-\infty}^{+\infty} t^n g(t) dt}{\int_{-\infty}^{+\infty} g(t) dt}$$

In certain cases, it may be advantageous to carry out an excitation by a light source, and a detection by the detection means, for 4 different pairs of positions of the radiation source and detection means.

It is then possible to:
select among the four pairs of positions the pair, known as fourth pair, for which the average arrival time of the photons, from the emitter to the receiver, is the shortest, and calculate, for this fourth pair of positions, the equation of a surface on which the fluorophore is situated;
and, for each of the three other pairs of positions, after calculation of a first equation of a surface on which the fluorophore is situated, it is possible to take a difference between this equation and that associated with the fourth pair, to obtain a second equation independent of the lifetime of the fluorophore.

It is thus possible, according to one embodiment, during step b) for each position pair, to calculate an equation for each surface, independent of the lifetime of the fluorophore, which may result from the difference between the average time calculated for each position pair and the average time calculated for another position pair. This other position pair may be that having a minimal average time or having a minimal calculated average time.

A method according to the invention may further comprise a visual or graphic representation of the position or the distribution of the fluorophore(s) or absorber(s).

The invention also relates to a method for localising a zone in a medium, comprising the introduction into said medium of at least one fluorophore or one absorber, and the localisation of this fluorophore or this absorber in said medium by a method according to the invention. The zone may be for example a medium constituted of a human or animal organ, the fluorophore or the absorber making it possible to label this zone. The aim may be to localise diseased cells in such a medium. As already indicated above, the invention enables this localisation to be carried out in a short time, or even in real time.

A method according to the invention may be implemented in an invasive or non-invasive manner.

The invention also relates to a device for implementing a method according to the invention, and enabling the localisation of a fluorophore in a scattering medium.

The invention also thus relates to a device for localising a fluorophore in a scattering medium, which may be one of the types evoked above, comprising:
at least one light or radiation source, suited to emitting an excitation radiation of this fluorophore,
at least one detection means suited to measuring a fluorescence signal ($\Phi_{fluo}$) emitted by this fluorophore,
calculation means, to calculate:
a) for each pair of positions among at least 3 different pairs of positions of a radiation source and detection means, the determination, after an excitation carried out by a radiation coming from the radiation source, and a detection by the detection means of the fluorescence signals emitted by this fluorophore after this excitation, of a surface on which the fluorophore is situated, or a volume comprising this surface and in which the fluorophore is situated,
b) an estimation of the localisation of the fluorophore in its surrounding medium, by calculation of the intersection of the three surfaces or a volume around this intersection.

The calculation means make it possible to calculate, for each position pair, a normalised time moment, of order n (n≧1), of a fluorescence time function. This moment may be obtained from a frequency function, deduced from said fluorescence time function for example by Fourier transform.

According to an advantageous embodiment, the calculation means enable, for each position pair, a calculation of an equation of each surface, independent of the lifetime of the fluorophore. To this end, the calculation means make it possible to take the difference between the average time calculated for each position pair and the average time calculated for another position pair.

DETAILED DESCRIPTION OF SPECIFIC EMBODIMENTS

Figure 1A:
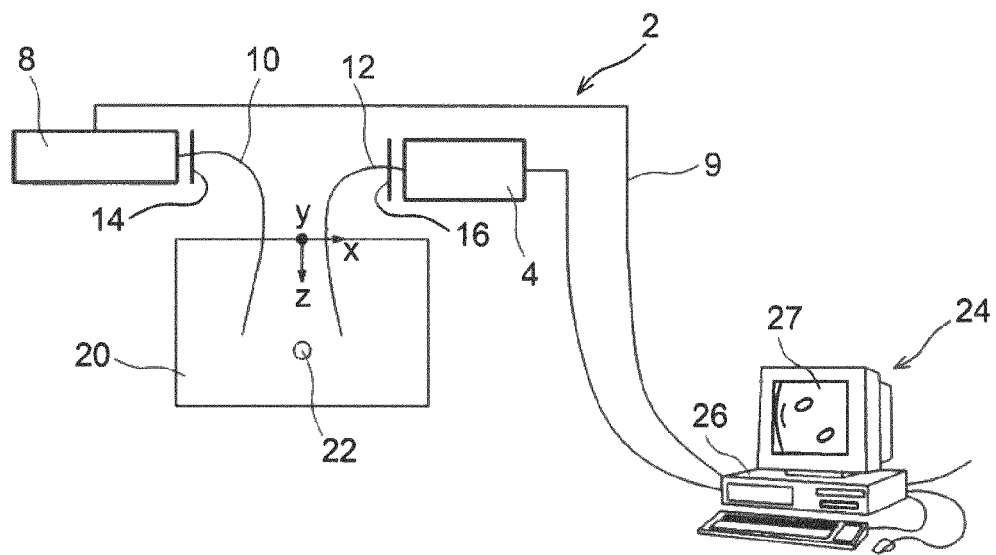
FIGS. 1A and 1B each represent an example of experimental device for the implementation of the invention.

FIG. 1A is an example of experimental system 2 to implement a method according to the invention. Schematic representations of a medium and excitation and detection means are given hereafter with reference to FIGS. 10A-10D.

The device of FIG. 1A uses as detector 4 a photomultiplier and a TCSPC (Time Correlated Single Photon Counting) card, in fact integrated in an assembly of data processing means 24.

The light is emitted by a radiation source 8 in pulses. The time of each pulse is generally less than 1 ns, for example between on the one hand several hundred fs, for example 500 fs, or 100 ps or 500 ps and on the other hand 100 ps or 500 ps or 1 ns. The repetition rate is preferably between several hundred kHz, for example 100 kHz or 500 kHz, and several hundred MHz, for example 100 MHz or 500 MHz.

The light emitted by the source 8 is sent and collected by fibres 10, 12 that may be moved. The two fibres may be assembled on vertical and horizontal translation movement means (along the axes X, Y and Z of FIG. 1A). To do this, it is possible to implement one or more plates assembled in translation to move the ends of the optic fibres. A laser may also be used, it also assembled on a plate assembled in translation. A detector may also be assembled on such a plate. In all cases, the translation may be computer controlled.

The source 8 of radiation pulses may also be used as means of triggering the TCSPC card (see the connection 9 between the source 8 and the means 24). It is also possible to work with pulses in the range of the femtosecond, providing that the appropriate radiation source is available, in other words a source laser 8, each pulse of which has a temporal width also in the range of the femtosecond.

According to a specific embodiment, the source 8 is a pulsed laser diode, for example at a wavelength close to 630 nm and with a repetition rate of around 50 MHz.

The laser light preferably passes through an interferential filter 14 to eliminate any secondary modes.

The fibre 12 collects the light coming from the studied medium 20, in particular the light diffused by this medium. An interferential filter 16 and/or a coloured filter absorbing low wavelengths may be placed in front of the detector 4 to select the fluorescence light (for example: $\lambda > 650$ nm, the source being at a wavelength of, for example, 631 nm) from a fluorophore 22 laid out in the medium 20 and to optimise the elimination of the excitation light.

In the text of the present application, whatever the embodiment of the invention, the position of the radiation source, and/or the position of the detection means will in particular be considered. When fibres are used, these positions are usually understood to be those of the ends of the fibres that bring the radiation into the scattering medium 20, or to the interface of this medium, and/or those that collect the diffused radiation, the latter being placed in the medium or at the interface of this medium, but are then not understood as being those of the actual source 8 or the actual detector 4.

Figure 1B:
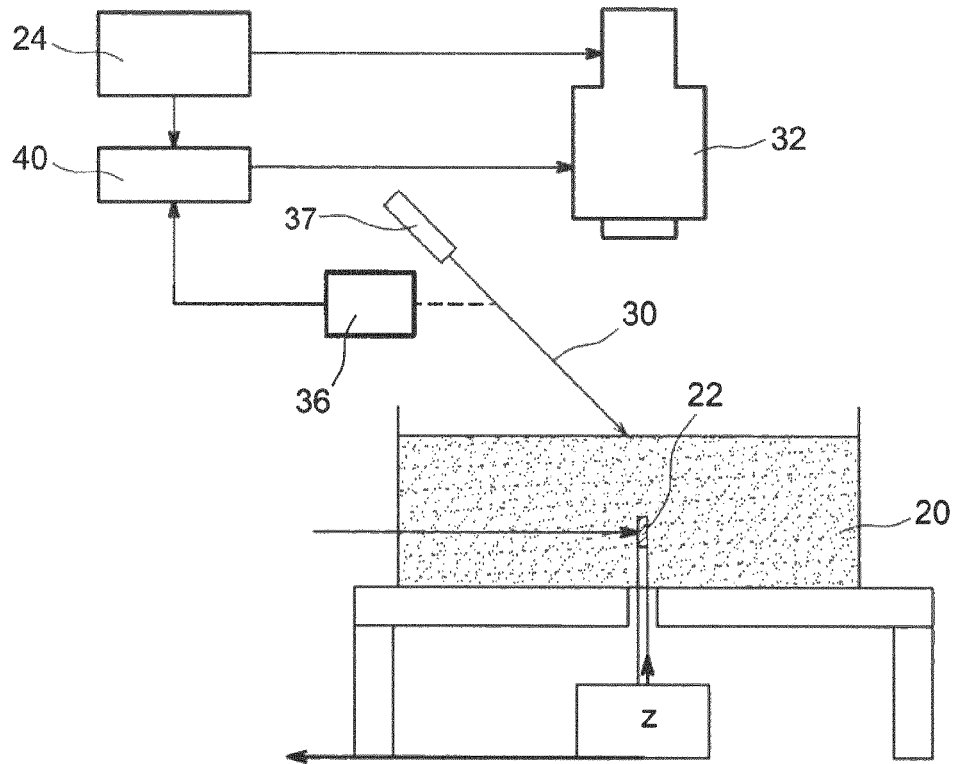

As an alternative, a light source delivering a light beam may be used, for example an emission laser, and a camera provided with an output objective, which enables an optical coupling between the sensitive face of the camera and the output face of the object observed (which is the case of the device of FIG. 1B).

In "endoscopy" type application, a fibre system is preferentially used, the fibres may be for example integrated in an endorectal probe, at least one fibre transmitting the light from the source of pulsed excitation light to the zone to be examined. This pulsed light source may be external to the probe. At least one other fibre transmits the emission optical signal from the zone to be examined to a photodetector, which can also be external to the probe. According to the TCSPC technique (for Time Correlated Single Photon Counting), a photon emitted by the fluorophore after a pulse of the radiation source is detected, by means of the photomultiplier.

The system thus enables a time resolved detection of fluorescence pulses. It enables fluorescence photons to be recovered.

Figure 2A:
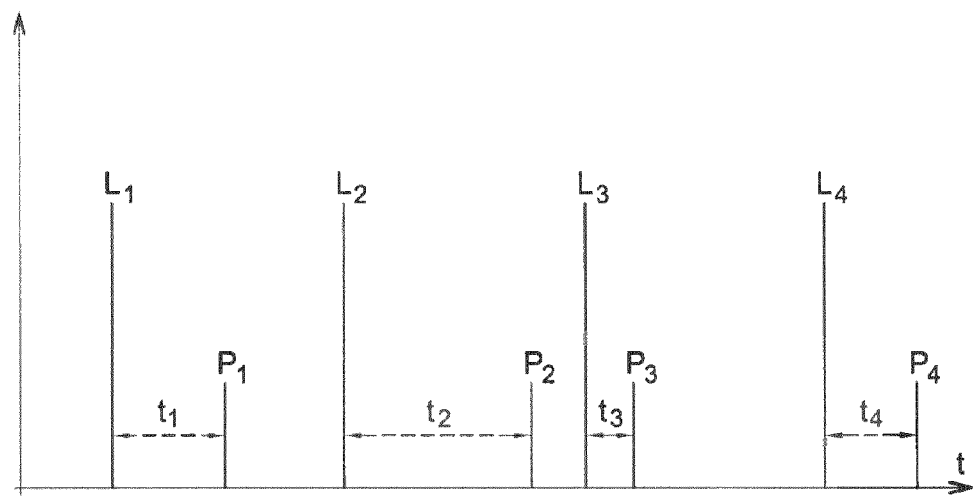
FIGS. 2A and 2B represent respectively a series of laser pulses and single photons emitted, and a fluorescence curve obtained from data relative to the single photons.

FIG. 2A represents a series of laser pulses $L_i$ (i=1-4) and a series of corresponding single photons $p_i$ (i=1-4), said photons being detected by a TCSPC (Time Correlated Single Photon Counting) type system. Each photon is in fact detected in relation to the departure of the corresponding pulse: in FIG. 2A, $t_i$ represents the time lapsed between each laser pulse $L_i$ and the instant of detection of each photon $p_i$.

Figure 2B:
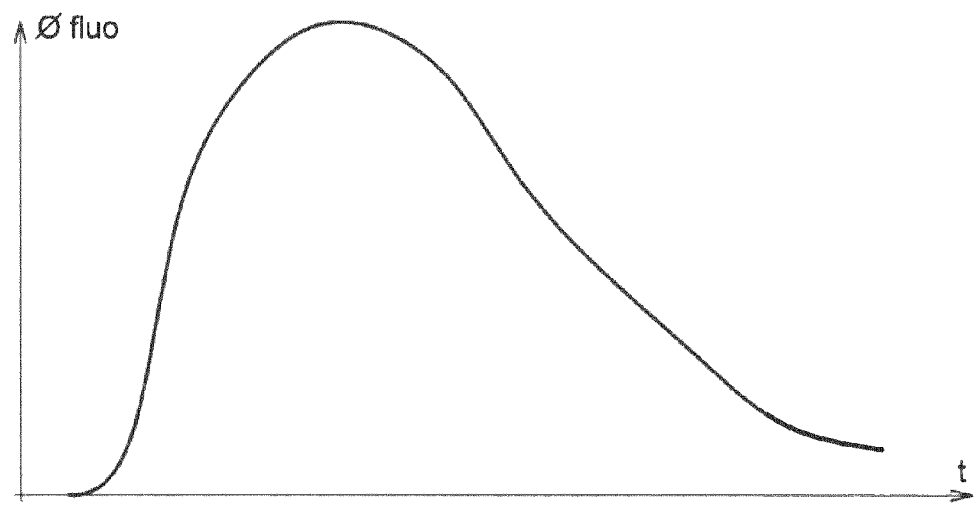

It is thus then possible to establish a statistical distribution or histogram of the arrival time of the photons, as illustrated in FIG. 2B, which represents the number of fluorescence photons detected, as a function of the time passed t in relation to each laser pulse. It is possible to determine, from such a histogram, statistical parameters, particularly an average of the arrival time, or average time (it is in fact the average of the abscissa weighted by the ordinates of the histogram).

Such a curve $\Phi_{fluo}$ (t) which, as can be seen (see also the example of FIG. 4C), makes it possible to use all the information over a wide time window, on either side of the maximum intensity point (and not only in the rising part of the signal), may thus then be processed so as to draw from it characteristic information, such as the arrival time, or average time as will be explained below.

Electronic means 24 such as a micro-computer or computer are programmed to memorise and process the data of the TCSPC card. More specifically, a central unit 26 is programmed to implement a processing method according to the invention. Display or visualisation means 27 make it possible, after processing, to represent the positioning of the fluorophore or fluorophores in the examined medium 20.

Other detection techniques may be employed, for example with an intensified camera, and for example an ultra-rapid intensified camera of "gated camera" type; in this case the camera opens in a time gate, of width for example around 200 ps, then this gate is shifted, for example from 25 ps to 25 ps.

FIG. 1B is an example of another experimental system 2 using as detector 32 a rapid camera: the relative position of the source (or the detector) and the object may be easily achieved.

An excitation beam 30 of the fluorescence of a medium 20, containing one or more fluorophores 22, is emitted by a radiation source 37 (not represented in the figure), which may be of the same type as that presented above with reference to FIG. 1A. A photodetector 36 makes it possible to control means 40 forming a delay line. The reference 24 designates, as in FIG. 1A, electronic data processing means of microcomputer or computer type, programmed to memorise and process the data from the camera 32. A central unit of these means 24 is programmed to implement a processing method according to the invention. Once again, display or visualisation means make it possible, after processing, to represent the positioning or the localisation of one or more fluorophores in the examined medium 20.

The distance between the light beam emitted by the source, and the detector, or the part of the medium optically coupled to the detector, is for example between several mm and several cm, for example between 1 mm and 20 cm in the case of biological media. This is the case in particular in the case of an an endorectal probe. The relative positioning of the source and the detector in relation to an organ to be examined may be determined by optical or ultrasonic type means, for example an ecography probe.

As an alternative of the above devices, it is possible to place a number n of light sources and a number p of detectors, with for example $1 \leq n \leq 3$ and $1 \leq p \leq 3$, the light sources and the detectors may be the ends of optic fibres connected respectively to at least one pulsed light source or at least one photodetector, of photomultiplier or camera type. These positions are then combined so as to have at least 3 distinct pairs of source positions and detector positions:

a source position S1 (case n=1) successively with 3 distinct detector positions D1, D2, D3 (case p=3); thus the position pairs (S1, D1), (S1, D2), (S1, D3) are used, two distinct positions S1 and S2 of the source (case n=2) with 2 or 3 distinct detector positions (case p=2 or 3); thus for example the position pairs (S1, D1), (S2, D2) and (S1, D2) or (S1, D1), (S2, D2) and (S1, D3) are used, three distinct positions S1, S2 and S3 of the source (case n=3) with 1 or 2 distinct detector positions (case p=1 or 2); thus for example the position pairs (S1, D1), (S2, D1) and (S3, D1) or (S1, D1), (S2, D2) and (S3, D2) are used.

Preferably, 3 pairs are used, for which the source positions are distinct from one another and the 3 detector positions are distinct from one another (configuration: (S1, D1), (S2, D2) and (S3, D3)).

The excitation light, at the wavelength $\lambda_x$ excites the fluorophore, which re-emits a light known as emission at the wavelength $\lambda_m > \lambda_x$ with a lifetime $\tau$. This lifetime corresponds to the average time during which the excited electrons remain in this state before returning to their initial state. The developments that follow show that the case of an absorber, and thus of an emission at wavelength substantially equal to that of excitation with a zero lifetime, may be deduced from the case of a fluorophore.

The propagation equation of the excitation light in a scattering medium produced by the pulsed radiation source radiation may be expressed as:

$$\frac{1}{c_n}\frac{\partial \phi_x(r,t)}{\partial t} + \vec{\nabla} \cdot (-D_x(r)\nabla \phi_x(r,t)) + \mu_{ax}(r)\phi_x(r,t) = S_x(r_s,t) \quad (1)$$

where
$r_s$ designates the position of the source,
r designates any position in the medium,
the function $\Phi_x(r, t)$ designates the intensity of radiation or the flux density of the excitation radiation at the point r at time t.
the coefficient $D_x(r)$ is the diffusion coefficient at the point r, at the excitation wavelength $\lambda x$
$S_x(r_s, t)$ designates the flux of radiation emitted, at time t, by the source at the point $r_s$.
That of the emission light may be expressed as:

$$\frac{1}{c_n}\frac{\partial \varphi_m(r,t)}{\partial t} + \vec{\nabla} \cdot (-D_m(r)\nabla \varphi_m(r,t)) + \mu_{am}(r)\varphi_m(r,t) = \quad (2)$$

$$\frac{1}{\tau}\eta\mu_{ax-->m}\int_0^t \exp\left(\frac{-(t-t')}{\tau}\right)\varphi_x(r,t')dt'$$

with:
the function $\Phi_m(r, t)$, which designates the intensity of radiation or flux density of the emission radiation at the point r at time t,
the coefficient $D_m(r)$, which is the diffusion coefficient at the point r at the emission wavelength $\lambda m$.
The conditions at the limits being as follows:

$$\phi_x(r,t) + 2AD_x(r)\frac{\partial \phi_x}{\partial n}(r,t) = 0 \quad (3)$$

$$\phi_m(r,t) + 2AD_m(r)\frac{\partial \phi_m}{\partial n}(r,t) = 0 \quad (4)$$

and this holds for any point r of the boundary $\delta\Omega$ of the scattering medium.

These equations are also developed and explained in the thesis of Aurélie Laidevant, "*Méthodes optiques résolues en temps pour la tomographie de fluorescence dans les milieux diffusants*" (Time-resolved optical methods for fluorescence tomography in diffusing media), Université Joseph Fourier, Grenoble, 5 Oct. 2006, p. 51 and following pages.

In these equations:

$\mu_{ax}$ and $\mu_{am}$ are the absorption coefficients of the scattering medium at the excitation $\lambda_x$ and emission $\lambda_m$ wavelength respectively, $\mu_{ax\_m}$ is the absorption coefficient associated with the local concentration of fluorophores at the excitation wavelength $\lambda_x$, $\eta$ is the quantum efficiency of the fluorophore, $\Phi(r,t)$ is the intensity of radiation or flux density associated with the density of photons, in photons/m²s, or, in an equivalent manner, in Watt/m², A is equal to $(1-R_{eff})/(1+R_{eff})$, where $R_{eff}$ is the reflection coefficient due to the index difference between air and the medium 22 surrounding the fluorophore.

The condition at the limits expresses that, at the boundary of the medium, the intensity of radiation or diffused flux density is zero.

The theoretical function $\Phi_m$ may be considered as proportional to the TPSF, the latter being measured experimentally (FIG. 2B). Thus, the normalised time moments of the TPSF are equal to the normalised time moments of the function $\Phi_m$.

The resolution of the system of coupled equations obtained is not easy, and the exploitation of the volume of data that the time signal contains is difficult. In general, the interest is in the exploitation of data, for example from such or such a time interval, extracted from these time dependent functions (known as TPSF for Temporal Spread Function) to carry out a step of 'fitting' with the experimental data.

To exploit the temporal information by means of other magnitudes, extracted from the measured TPSF, other measures may be defined such as the measure of moments—Mellin transforms of the TPSF, or Fourier transforms (and thus work in frequency mode), or Laplace transforms or by parameterisation of the TPSF (in other words the determination of characteristic parameters such as the coordinates of the maximum, and/or the up slope and/or down slope coefficient of the TPSF). The interest of such magnitudes is to reduce the volume of data by eliminating any redundancies that may exist between them.

In the remainder of the invention, the main interest lies in the calculation of n order moments of the histogram, such a calculation being able to be carried out by Fourier transform.

In particular, it is possible, beginning with the function $\Phi_m$, to calculate any normalised time moment, and particularly the normalised 1$^{st}$ order moment. Such a magnitude corresponds to the average arrival time of the photons. The normalised time moments of the function $\Phi_m$ are defined as:

$$m_k = \int_{-\infty}^{+\infty} t^k \phi_m(r,t) dt \bigg/ \int_{-\infty}^{+\infty} \phi_m(r,t) dt \qquad (6)$$

The 0 order moment is:

$$m_0 = \int_{-\infty}^{+\infty} \phi_m(r,t) dt$$

The case of an infinite medium will now be considered. It can be shown that the normalised 1$^{st}$ order time moment of the function $\Phi_m$, defining the average arrival time of the photons $<t>\infty$, in infinite medium is expressed:

$$m_1 = \int_{-\infty}^{+\infty} t\phi_m(r,t) dt \bigg/ \int_{-\infty}^{\infty} \phi_m(r,t) dt = <t>_\infty = \qquad (7)$$

-continued
$$<t>_x + <t>_m + <t>_{fluo} = \frac{r_{sr}}{2c_n\sqrt{\mu_{ax} D_x}} + \frac{r_{rd}}{2c_n\sqrt{\mu_{am} D_m}} + \tau$$

where $<t>_x$, $<t>_m$ and $<t>_{fluo}$ designate respectively the average time of the source-fluorophore trajectory, the time of the fluorophore-detector trajectory, and the average lifetime of the excited species (the latter being equal to 0 in the presence of an absorber). Furthermore, it will be recalled that:

$r_{sr}=|r_s-r|$ $r_{rd}=|r-r_d|$ $m_1$ is the result of the measurement

It will be seen that this is the equation of a 3D surface, here having the shape of an ellipsoid.

More generally, the normalised moment of order k may be expressed in the form:

$$m_k = (i)^k \frac{\partial^k \tilde{\Phi}(\omega)}{\partial \omega^k} \bigg| \omega = 0 \times \frac{1}{\tilde{\Phi}(\omega) | \omega = 0} \qquad (8)$$

Where $\tilde{\Phi}(\omega)$ is the Fourier transform of $\Phi_m$:

$$\tilde{\Phi}(\omega) = \frac{1}{\sqrt{2\pi}} \int_{-\infty}^{+\infty} \phi(t) e^{-i\omega t} dt$$

$$\frac{\partial \tilde{\Phi}(\omega)}{\partial \omega} = \frac{-i}{\sqrt{2\pi}} \int_{-\infty}^{+\infty} t\phi(t) e^{-i\omega t} dt$$

For example, it can be shown that the variance of the time distribution may be expressed as $V=<(t-<t>)^2>=m_2-m_1^2$, i.e. in infinite medium $$V = \frac{r_{sr}}{2c_n^2 \sqrt{\mu_{ax}^3 D_x}} + \frac{r_{rd}}{2c_n^2 \sqrt{\mu_{am}^3 D_m}} + \tau^2.$$

It is thus observed that one obtains, also in the case of the variance, the definition of a three-dimensional surface, here, that of an ellipsoid.

This magnitude (the variance) may be calculated within the scope of the present invention from 2$^{nd}$ and 1$^{st}$ order moments.

More generally still, it is possible, according to the invention, to calculate any order moment greater than 1, and to establish a relation linking at least one of these moments to the respective source-fluorophore and fluorophore-detector distances. If higher order moments are considered, the equation linking the latter, or a combination of the latter, at the respective source-fluorophore and fluorophore-detector distances, is also that of a three-dimensional surface.

Preferentially, the normalised 1$^{st}$ order moment is used.

Generally speaking, a fluorophore may be seen as capable of absorbing a certain quantity of light (in its excited state) and re-emitting part of it at a higher wavelength (during its de-excitation), with a delay corresponding to the time spent in the excited state. From the expressions given above, it is thus possible to go from the case of the fluorophore to the absorber simply by writing $\mu_{ax}=\mu_{am}$, $D_x=D_m$ and $\tau=0$. This holds for all of the cases disclosed in the present application. The above considerations thus also hold for the case of an absorbing object.

The infinite medium is typically that which is encountered when invasive measures are carried out, with fibres 10, 12 to bring the light into a medium 21 (case of FIG. 10A) and to withdraw the fluorescence signal emitted by the fluorophore F, the ends of the fibres being positioned in the scattering medium, each at a distance $d_{10}$ and $d_{12}$ of at least 1 cm or 1.5 cm from a wall 21 that delimits the medium. More generally, it is possible to consider that one is in an infinite medium when the source and the detector are placed at a sufficient depth in the scattering medium. In practice, this corresponds to invasive measures, carried out by laying out for example optic fibres, or a part of these fibres, inside a scattering medium.

A first hypothesis is considered, that of a medium where the optical properties are identical at the 2 excitation and measure wavelengths, $\lambda_x$ and at $\lambda_m$, which is for example substantially the case when these two wavelengths are for example 10 nm or several tens of nm distant from each other. It should also be recalled that $\lambda x = \lambda m$ when there is only one non-fluorescent absorber. The optical properties of the medium at the two wavelengths may thus be considered as identical. There is then a simplification of the above equation (7):

$$r_{sr} + r_{rd} = 2c_n\sqrt{\mu_a D}(<t>_\infty - \tau) \quad (9)$$

This constitutes the formula of an ellipsoid of focus or centres S and D, i.e. the place of points r such that the source-fluorophore distance $r_{sr}$ plus the fluorophore-detector distance $r_{rd}$ is equal to the product of the apparent velocity in the scattering medium $2c_n\sqrt{\mu_a D}$ multiplied by the average arrival time of the photons corrected for the delay introduced by the lifetime $\tau$.

Thus, to find the 3D position of the fluorophore, it is sufficient to take 3 measures at three source positions and 3 detector positions. The fluorophore is thus at the intersection of 3 ellipsoids defined in space by 3 different equations. Preferably, position pairs defining directions substantially perpendicular to one another are selected. For each pair, a TPSF or a histogram are established as explained above.

In the second hypothesis, the case where the optical properties cannot be considered identical at the 2 wavelengths, the equation (7) becomes:

$$\boxed{\begin{aligned}\frac{r_{sr}}{v_x} + \frac{r_{rd}}{v_m} &= <t>_x + <t>_m = (<t>_\infty - \tau) \\ v_{x,m} &= 2c_n\sqrt{\mu_{ax,m} D_{x,m}}\end{aligned}} \quad (10)$$

This is still the equation of an ellipsoid but it now expresses the place of points r such that the source-fluorophore distance $r_{sr}$ is "weighted" by the apparent velocity $v_x$ (from where the term $r_{sr}/v_x$ comes), and the fluorophore-detector distance $r_{rd}$ is "weighted" by the apparent velocity $v_m$ (from where the term $r_{rd}/v_m$ comes).

Once again, to find the 3D position of the fluorophore, 3 measures at three source positions and 3 detector positions are taken. The fluorophore is thus at the intersection of 3 ellipsoids defined in space by different equations. Preferably, position pairs defining directions substantially perpendicular to one another are selected. For each position pair (source, detector), a TPSF or a histogram is established as explained above. Also preferably, during each acquisition, it will be attempted to increase as much as possible the source-detector distance.

The expressions of the average times may be given analytically for geometries other than those of the more complex, infinite medium: semi-infinite medium, with an interface plane; planar medium with parallel faces, etc.

Generally speaking, if the expression, whether analytical or numerical, of the Fourier transform $\tilde{\Phi}(\omega)$ of the function $\phi_m$ is known, then:

$$m_1 = <t> = i\frac{\partial \tilde{\Phi}(\omega)}{\partial \omega}\bigg|\omega = 0 \times \frac{1}{\tilde{\Phi}(\omega)|\omega = 0},$$

Where $\frac{\partial \tilde{\Phi}(\omega)}{\partial \omega} = \frac{-i}{\sqrt{2\pi}}\int_{-\infty}^{+\infty} t\phi(t)e^{-i\omega t}dt$ $$\tilde{\Phi}(\omega) = \frac{1}{\sqrt{2\pi}}\int_{-\infty}^{+\infty} \phi(t)e^{-i\omega t}dt$$

The surface described is no longer an ellipsoid, but remains a 3D surface; thus, once again, a fluorophore is localised by searching for intersections between 3 surfaces, each obtained for a different (source position, measure position) pair.

Generally speaking, in all of the cases concerned by the invention (those above and the others set forth below), to find the 3D position of the fluorophore, 3 measures are taken with three positions, preferably different to each other, of sources and 3 positions, preferably different to each other, of detectors (in other words, one measure for each of the 3 pairs ($r_{si}$, $r_{di}$), i=1, 2, 3, with $r_{si} \neq r_{sj}$ for i≠j and $r_{di} \neq r_{dj}$, for i≠j). The fluorophore is thus at the intersection of 3 ellipsoids defined in space by 3 different equations. Preferably, 3 position pairs defining directions substantially perpendicular to one another are selected. In certain cases, an example of which will be given later, it may be necessary to take 4 measures for 4 position pairs (source, detector). For each position pair (source, detector), a TPSF or histogram is established as explained above.

Another example is the case of a semi-infinite medium. This is the case of any surface-probed organ, for example prostate, breast, brain, the thickness of which is sufficiently high given the characteristic source-detector distances.

Figure 10A:
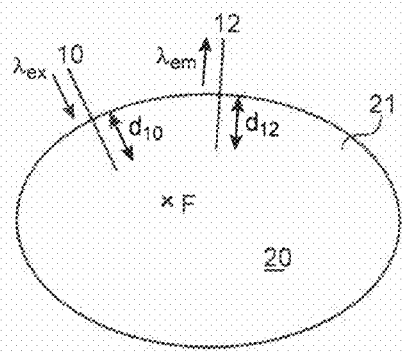
FIGS. 10A-10D represent various lay outs, in relation to a studied medium, of excitation and detection means, or of optic fibres bringing to this medium an excitation radiation and transmitting a radiation to be detected.
Figure 10B:
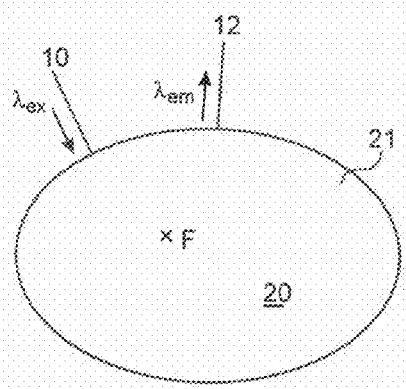
Figure 10C:
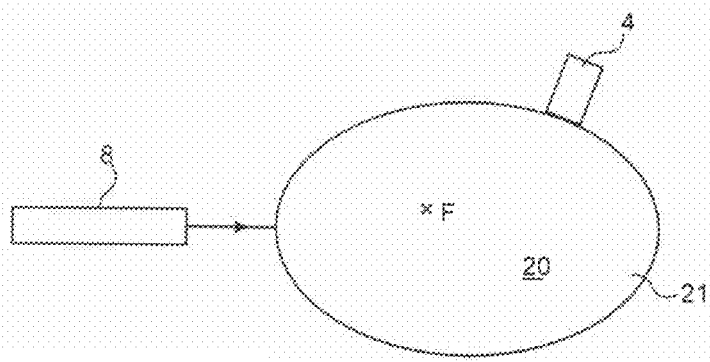

This case is that which is encountered when measures are taken, with fibres 10, 12 to bring in the light and to receive or sample the fluorescence signal, the ends of the fibres being positioned at the surface of a wall 21 that delimits the medium (FIG. 10B). More generally, it is the case where source and detector are positioned at the surface of this wall 21 that delimits the scattering medium in which the fluorophore F is laid out.

This is particularly the case when it is wished to be non-invasive, source and detector being positioned near to the surface of the medium. Thus, in the case of a diagnosis of a tumour of the prostate, source and detector will be placed round the edge of an endorectal probe.

It involves in this case confirming not only the propagation equation but also the corresponding boundary conditions, already indicated above:

$$\phi(r, t) + 2AD(r)\frac{\partial \phi}{\partial n}(r, t) = 0,$$

for any point r of the boundary $\delta\Omega$ of the scattering medium, and this for excitation and emission wavelengths.

It can be shown that this condition is equivalent to writing, in a more simple manner, $\phi(r,t)=0 \, \forall r \in \partial\Omega_{extrapolated}$, where the extrapolated boundary is situated at a distance $d_{extrapolated}=2AD$ from the physical boundary, as explained in the article of A. Laidevant et al. "Effects of the surface boundary on the determination of the optical properties of a turbid medium with time resolved reflectance", Applied Optics, 45, 19, 4756 (2006).

One way of satisfying this condition is to use the image sources method, as mentioned in the above article, but also as explained in the thesis of Aurélie Laidevant, "*Méthodes optiques résolues en temps pour la tomographie de fluorescence dans les milieux diffusants*" (Time-resolved optical methods for fluorescence tomography in turbid media), Université Joseph Fourier, Grenoble, 5 Oct. 2006, p. 55-56:

the solution in infinite medium for a source placed in r+ is known. One way of satisfying $\phi(r,t)=0 \ \forall r \in \partial\Omega_{extrapolated}$ is to place a virtual source, of negative contribution, at a position r−, symmetrical with r+ in relation to the extrapolated boundary $\partial\Omega_{extrapolated}$.

And all of this is also valid in the frequency domain, and one has:

$$\tilde{\Phi}^{1/2\infty}(\omega) = \tilde{\Phi}^{\infty+}(\omega) - \tilde{\Phi}^{\infty-}(\omega) =$$

$$\frac{1}{4\pi c_n D}\left[\frac{e^{ik(\omega)r_+}}{r_+} - \frac{e^{ik(\omega)r_-}}{r_-}\right] = \frac{1}{4\pi c_n D}[G^{\infty}(k(\omega), r_+) - G^{\infty}(k(\omega), r_-)]$$

with:

$$k^2(\omega) = -\frac{\mu_a}{D} + i\frac{\omega}{c_n D}$$

and:

$\tilde{\Phi}^{\infty+}$: Fourier transform of the intensity of radiation or flux density emitted by the positive source in the hypothesis of an infinite medium.

$\tilde{\Phi}^{\infty-}$: Fourier transform of the intensity of radiation or flux density emitted by the negative source in the hypothesis of an infinite medium $r_+ = |r_s^+ - r|$ distance to the positive excitation source, the positive excitation source being the excitation source $r_- = |r_s^- - r|$: distance to the negative excitation source, this negative source being dummy, and defined in order to obtain $\phi(r,t)=0 \ \forall r \in \partial\Omega_{extrapolated}$.

$r_{s+}$: coordinates of the positive excitation source $r_{s-}$: coordinates of the negative excitation source $G^{\infty}(k(\omega),r)$: Green's function satisfying the diffusion equation in infinite medium.

$$G^{\infty}(k(\omega), r) = \frac{e^{ik(\omega)r}}{r}$$

Furthermore, it has been seen that $$m_1 = <t> = i\frac{\partial \tilde{\Phi}(\omega)}{\partial \omega}\bigg|_{\omega=0} \times \frac{1}{\tilde{\Phi}(\omega)|_{\omega=0}}$$

One deduces from this, for the semi-infinite medium:

$$<t>_{x,1/2\infty} = \frac{1}{2c_n\sqrt{\mu_{ax}D_x}} \frac{\frac{e^{ik(0)r_+}}{r_+} - \frac{e^{ik(0)r_-}}{r_-}}{\frac{e^{ik(0)r_+}}{r_+} - \frac{e^{ik(0)r_-}}{r_-}} =$$

$$\frac{1}{2c_n\sqrt{\mu_{ax}D_x}} \frac{\frac{e^{-\sqrt{\frac{\mu_{ax}}{D_x}}|r_{s+}-r|}}{|r_{s+}-r|} - \frac{e^{-\sqrt{\frac{\mu_{ax}}{D_x}}|r_{s-}-r|}}{|r_{s-}-r|}}{\frac{e^{-\sqrt{\frac{\mu_{ax}}{D_x}}|r_{s+}-r|}}{|r_{s+}-r|} - \frac{e^{-\sqrt{\frac{\mu_{ax}}{D_x}}|r_{s-}-r|}}{|r_{s-}-r|}} =$$

$$\frac{f(|r_{s+}-r|, |r_{s-}-r|, k_x(0))}{2c_n\sqrt{\mu_{ax}D_x}} \Leftrightarrow$$

$$\boxed{<t>_{x,1/2\infty} = \frac{1}{2c_n\sqrt{\mu_a D}} \frac{r_+ G^{\infty}(k(0), r_+) - r_- G^{\infty}(k(0), r_-)}{G^{\infty}(k(0), r_+) - G^{\infty}(k(0), r_-)}}$$

In the same way, it can be shown that $$<t>_{m,1/2\infty} = \frac{1}{2c_n\sqrt{\mu_{am}D_m}} \frac{\frac{e^{ik(0)r'_+}}{r'_+} - \frac{e^{ik(0)r'_-}}{r'_-}}{\frac{e^{ik(0)r'_+}}{r'_+} - \frac{e^{ik(0)r'_-}}{r'_-}} =$$

$$\frac{1}{2c_n\sqrt{\mu_{am}D_m}} \frac{\frac{e^{-\sqrt{\frac{\mu_{am}}{D_m}}|r_{d+}-r|}}{|r_{d+}-r|} - \frac{e^{-\sqrt{\frac{\mu_{am}}{D_m}}|r_{d-}-r|}}{|r_{d-}-r|}}{\frac{e^{-\sqrt{\frac{\mu_{am}}{D_m}}|r_{d+}-r|}}{|r_{d+}-r|} - \frac{e^{-\sqrt{\frac{\mu_{am}}{D_m}}|r_{d-}-r|}}{|r_{d-}-r|}} =$$

$$\frac{f(|r_{d+}-r|, |r_{d-}-r|, k_m(0))}{2c_n\sqrt{\mu_{am}D_m}} \Leftrightarrow$$

With:

$r_d^+$: position of the positive source, which is in this case the fluorescent source $r_d^-$: position of the negative source of the fluorescent source, dummy source making it possible to obtain $\phi_m(r,t)=0 \ \forall r \in \partial\Omega_{extrapolated}$ $r'+ = |r_d^+ - r|$ = distance to the positive fluorescent source $r'- = |r_d^- - r|$ = distance to the negative fluorescent source The use of a source image in semi-infinite medium is also described in the article of M. S. Paterson et al. "Time resolved reflectance and transmittance for the non-invasive measurement of tissue optical properties", Applied Optics, vol. 28, p. 2331-2336, 1989. This document also deals with a "slab" shape geometry.

It can be shown that for the fluorescence signal, the following equation still holds:

$$\boxed{<t>_{1/2\infty} = <t>_{x,1/2\infty} + <t>_{m,1/2\infty} + \tau = \frac{f(|r_{s+}-r|, |r_{s-}-r|, k_x(0))}{v_x} + \frac{f(|r-r_{d+}|, |r-r_{d-}|, k_m(0))}{v_m} + \tau}$$

This defines an implicit function and a surface in space in three dimensions.

Once again, and as already explained above, to find the 3D position of the fluorophore, 3 measures are taken at three source positions and 3 detector positions. The fluorophore is thus at the intersection of 3 surfaces defined in space by 3 different equations. For each position pair, a TPSF or a histogram is established as explained above.

Preferably, position pairs defining directions substantially perpendicular to each other are selected.

In practice, the conditions that define the geometry in semi-infinite medium are not very different to those of the infinite medium, from the moment that the source and the detector (in the case of FIG. 1A, the ends of the fibres 10 and 12) are positioned far from the interface, at more than 1 cm or 2 cm from it (as in FIG. 10A). In this case, indeed, everything takes place as if the medium were infinite, from the point of view of the fluorophore.

It is possible to confirm the validity of the equation $$<t>_{1/2\infty} = <t>_{x,1/2\infty} + <t>_{m,1/2\infty} + \tau =$$
$$\frac{f(|r_{s+} - r|, |r_{s-} - r|, k_x(0))}{v_x} + \frac{f(|r - r_{d+}|, |r - r_{d-}|, k_m(0))}{v_m} + \tau$$

if considered in the case of an infinite geometry. There is no fictive source and thus:

$r_{s+} = r_s$,
$r_- = |r_{s_-} - r| = +\infty$,
$r'^- = |r - r_{d_-}| = +\infty$,
$r_{d+} = r_d$ The expression corresponding to the infinite medium is then found again.

The case of a medium with parallel faces ("slab" shape geometry) will now be considered. This type of geometry is already mentioned in the article of M. S. Paterson et al. already cited above.

In this case, it is shown that, for the excitation signal:

$$\tilde{\Phi}_x^{slab}(\omega) =$$
$$\sum_i [\tilde{\Phi}_x^{\infty+}(r_{s+,i}, \omega) - \tilde{\Phi}_x^{\infty-}(r_{s-,i}, \omega)] = \frac{1}{4\pi c_n D_x} \sum_i \left[\frac{e^{ik(\omega)r_{i+}}}{r_{i+}} - \frac{e^{ik(\omega)r_{i-}}}{r_{i-}}\right]$$

The summation in this expression results from the fact that one is in the presence of two parallel planes that limit the medium. There is thus contribution of two negative virtual sources, but each of the two planes multiplies the effects of the negative virtual source associated with the other plane. It is thus necessary to add the contribution of these different effects, in the form of a sum to infinity indexed by i.

In an analogous manner, for the emission signal:

$$\tilde{\Phi}_m^{slab}(\omega) =$$
$$\sum_i [\tilde{\Phi}_m^{\infty+}(r'_{+,i}, \omega) - \tilde{\Phi}_m^{\infty-}(r'_{-,i}, \omega)] = \frac{1}{4\pi c_n D_m} \sum_i \left[\frac{e^{ik(\omega)r'_{+i}}}{r'_{+i}} - \frac{e^{ik(\omega)r'_{-i}}}{r'_{-i}}\right]$$

$<t>_{slab}$ designates the normalised moment of order 1 of $\Phi^{slab}(t)$ which can be obtained by the Fourier transform $\tilde{\Phi}^{slab}(\omega)$ and:

$$m_1 = <t> = i\frac{\partial \tilde{\Phi}slab(\omega)}{\partial \omega}\bigg|_{\omega=0} \times \frac{1}{\tilde{\Phi}slab(\omega)|\omega=0}:$$

$$<t>_x^{slab} = \frac{1}{2c_n\sqrt{\mu_{a_x}D_x}} \sum_i \frac{r_{+,i}G^\infty(k(0), r_{+,i}) - r_{-,i}G^\infty(k(0), r_{-,i})}{G^\infty(k(0), r_{+,i}) - G^\infty(k(0), r_{-,i})} =$$

$$\sum_i \frac{f(|r_{s+,i} - r|, |r_{s-,i} - r|, k(0))}{2c_n\sqrt{\mu_{a_x}D_x}}$$

and $$<t>_m^{slab} = \frac{1}{2c_n\sqrt{\mu_{a_m}D_m}} \sum_i \frac{r'_{+,i}G^\infty(k(0), r'_{+,i}) - r'_{-,i}G^\infty(k(0), r'_{-,i})}{G^\infty(k(0), r'_{+,i}) - G^\infty(k(0), r'_{-,i})} =$$

$$\sum_i \frac{f(|r_{d+,i} - r|, |r_{d-,i} - r|, k(0))}{2c_n\sqrt{\mu_{a_m}D_m}}$$

Or, $$<t>_{1/2\infty}^{slab} = <t>_{x,1/2\infty}^{slab} + <t>_{m,1/2\infty}^{slab} + \tau$$

I.e.:

$$<t>_{slab} =$$
$$\sum_i \left[\frac{f(|r_{si+} - r|, |r_{si-} - r|, k_x(0))}{v_x} + \frac{f(|r - r_{di+}|, |r - r_{di-}|, k_m(0))}{v_m}\right] + \tau$$

In practice however, for media of sufficient thickness, the sum converges quite quickly, for example when i is equal to 10 or close to 10, for example i=8, 9, 11 or 12.

The surface described is again a 3D surface. Thus, once again, a fluorophore is localised by searching for intersections between 3 surfaces, each obtained for a different (source position, measure position) pair.

To find the 3D position of the fluorophore, 3 measures are taken with three different positions of sources and 3 different positions of detectors, as already explained above.

The case of a medium of any shape will now be considered: this medium is limited by an envelope, but its shape is a priori undetermined. The most general method to deal with this case is the following.

A gridding of the medium is firstly carried out.

The equations are then resolved in a numerical manner (for example by the finite volume method, or the finite element method, etc.).

The fluorescence signal may be expressed in the following manner:

$\Phi_m(r_s,r_d,r,t) \propto \phi_x(r_s,r,t) * F(t) * \phi_m(r,r_d,t)$, where:

$$F(t) = \frac{e^{-t/\tau}}{\tau},$$

$$\frac{1}{c_n}\frac{\partial \phi_x(r, t)}{\partial t} + \vec{\nabla} \cdot (-D_x(r)\nabla \phi_x(r, t)) + \mu_{ax}(r)\phi_x(r, t) = \delta(r_s - r)\delta(t),$$

with the above boundary condition (3).

And:

$$\frac{1}{c_n}\frac{\partial \phi_m(r, t)}{\partial t} + \vec{\nabla} \cdot (-D_m(r)\nabla \phi_m(r, t)) + \mu_{am}(r)\phi_m(r, t) = \delta(r_d - r)\delta(t),$$

with the above boundary condition (4).

One thus obtains in this way, at all points r the value of the functions $\phi_x(r_s,r,t)$ and $\phi_m(r,r_d,t)$, for which it is possible to calculate the values of the moments, also at all points r, by applying the above relation (11).

One thus has the relation:

$$< t >_{signal\ measured}\ =\ < t >_x + < t >_m + < t >_{fluo}$$
$$=f'(|r_s-r|)+f'(|r-r_d|)+\tau,$$

where the functions f' are thus calculated numerically. One then searches for the points r such that this relation is true.

The parameters D and µ may be included in the function f' and thereby obtain the expression:

$$<t>_{signal\ measured}=f_x'(Dx,\mu ax,abs(rs-r))+f_m'(Dm,\mu am,|r-rd|)+\tau,$$

with:

$f_x'(Dx, \mu ax, |rs-r|)$: solution of the excitation equation
$f_m'(Dm, \mu am, |r-rd|)$: solution of the emission equation.

By numerical resolution, one finds points r that satisfy this equation and a surface passing through all of these points may be defined, for example by interpolation from one point to another. This surface is not necessarily an ellipsoid.

Finally, the case may be dealt with where the medium is not homogeneous from the point of view of its optical properties, which then become dependent on r. In this case, as in the case of a homogeneous medium of any shape, the numerical resolution of 3 equations is carried out, and the pair of points satisfying the three equations is identified.

The expression of $\tilde{\Phi}(\omega)$ for this medium, satisfying the diffusion equation written in the frequency domain is then determined numerically:

$$\vec{\nabla}\cdot(-D(r)\nabla\tilde{\Phi}(r,\omega))+\left(\mu_a(r)-\frac{i\omega}{c_n}\right)\tilde{\Phi}(r,\omega)=S(r_s)$$

And from this is then deduced $$<t>=i\frac{\partial\tilde{\Phi}(\omega)}{\partial\omega}\bigg|_{\omega=0}\times\frac{1}{\tilde{\Phi}(\omega)|_{\omega=0}}$$

Whatever the geometry envisaged, it is possible to dispense with the dependency in relation to the lifetime τ, by carrying out a 4$^{th}$ measure with a 4$^{th}$ position pair (position of the source, position of the detector) different to each of the preceding 3. For an additional pair of positions (source, detector), a TPSF or a histogram is established as explained above. The equation of a 4$^{th}$ surface is then obtained.

As indicated above in each of the cases considered, in fact a calculation of the average time is obtained from each fluorescence signal.

Document EP 1 884 765 discloses that the calculation of a variable independent of τ may be carried out by taking the difference between the average time calculated for each fluorescence signal and the average time calculated for a particular fluorescence signal, for example the particular fluorescence signal is that having a minimal average time or having a minimal calculated average time.

Among the 4 measures carried out for the 4 position pairs, that which corresponds to a minimal measured average time could be selected. The equation of the surface that corresponds to this minimal measure will be subtracted from each of the 3 other equations.

Then 3 new equations of 3 new surfaces are obtained, which may not be ellipsoids, but at the intersection of which will be localised the fluorophore, or even the fluorophore will be localised in a volume that contains this intersection.

Whatever the geometry envisaged, the calculation of the intersection of 3 ellipsoids, or 3 surfaces, defined in space by 3 different equations is carried out by means of a digital processing implemented by a computer, for example the means 24 of FIGS. 1A and 1B. This processing leads to a localisation of the intersection of the 3 surfaces with a certain precision. In other words, the resolution of the system of equations that constitute the definitions of the 3 surfaces is carried out with a certain precision, which will give an approximate solution: the fluorophore is then not localised exactly at the intersection of 3 surfaces, but in the vicinity of this intersection.

After having found a solution with a first precision, the calculation may be carried out again to find another solution with a second precision different from the first one.

Each surface can itself be defined with a certain precision. This no longer strictly speaking defines a surface, but a volume that depends on said surface. In the case of an ellipsoid, it may be an ellipsoidal crown. This volume is delimited by two surfaces, substantially parallel to the surface defined strictly by the corresponding equation and close to this, the proximity being defined by the precision associated with the surface, which should preferably be less than 25%, and even preferably less than ±10%. In other words, the intersection of 3 surfaces is not sought, but 3 volumes. This results not in a single point, but the identification of a volume, in general sufficiently small to be compatible with the localisation with a certain uncertainty; this volume contains the intersection of the 3 surfaces such as defined strictly by the 3 initial equations.

Generally speaking, different types of analysis may be distinguished.

There is firstly the case of an invasive analysis for which source and detector are placed inside the scattering medium. If the depth of the source and the detector in relation to the boundary of the medium is sufficient, it will be considered that the conditions of an infinite medium are met (case of FIG. 10A).

A first non-invasive analysis case is that for which source and detector are placed in contact with a boundary of the scattering medium (case of FIG. 10B).

A second case of non-invasive analysis is that for which source and detector are not in physical contact with a boundary 21 of the scattering medium 20, but are in optical contact with the medium. In this case, the source is for example a laser 8 focused on the surface 21 of the medium and the detector is a photodetector 4 in optical contact with the surface of the medium (case of FIG. 10C).

Figure 10D:
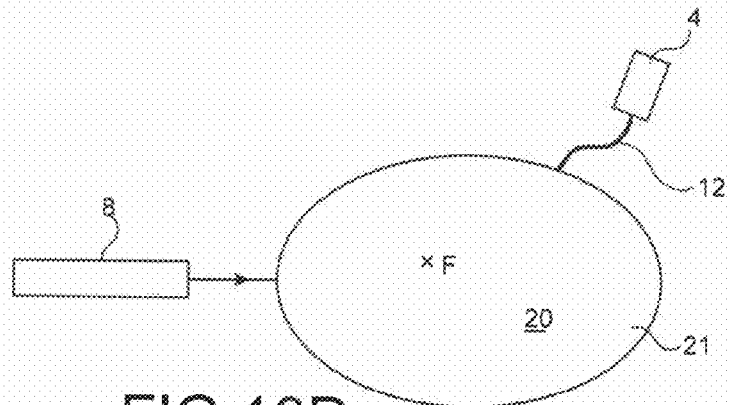

The first non-invasive case may be combined with the second non-invasive case, the source 8 being situated at a distance (such as the laser 8 of FIG. 10D) and the detection taking place at the contact, for example by means of an optic fibre 12, which brings the radiation to be detected to the detector 4 (case of FIG. 10D). Moreover, the excitation may take place at the contact, for example by means of optic fibres. Generally, in non-invasive mode, it is not considered that one is in an infinite geometry, and another type of geometry is then chosen:

semi-infinite geometry,
or slab type geometry,
or geometry of any shape.

The interest of moving closer to infinite, semi-infinite or slab type geometry is to make it possible to use an analytical relation linking a magnitude measured (for example the average arrival time of the photons) at the respective source— fluorophore (or aggregation or local accumulation of fluorophore) and detector—fluorophore (or aggregation or local accumulation of fluorophore) distances. Thus, for 3 different acquisitions, in other words carried out with 3 different pairs (source—detector), the problem comes down to determining the solutions satisfying the three analytical equations, which may be undertaken rapidly by means of current computation means. On the other hand, as described below, the fact of placing oneself in any geometry comes down to resolving the problem in a digital manner, to the detriment of the calculation time.

In the different cases explained above with reference to FIGS. 10A-10D, the reference 20 designates a studied medium, the limit of which is the wall 21. This medium 20 may be for example an organ of an animal or a human being, for example the brain, or a breast (as examples of fluorophores for these different media, indocyanine green, or fluorescein may be cited).

In these figures, the point F designates a fluorophore or an aggregation of fluorophores. But it will be recalled that it may also be an absorber (or again a fluorophore re-emitting at the same energy as that of excitation, and with a time $\tau=0$) or an aggregation of absorbers. In this case, the medium 20 may instead be an organ, the zone F identifying a cancerous tumour, visible by the simple fact that it has a higher attenuation coefficient than the surrounding healthy tissues.

Examples will now be described.

EXAMPLES

Example I

This example is a calculation in two dimensions. It thus does not relate to a real measure, but illustrates the method in a theoretical case, in a plane.

The medium is assumed infinite, in 2 dimensions, with the following optical properties.

The reduced diffusion coefficient is $\mu'_s=10$ cm$^{-1}$ which leads to: $D=\frac{1}{3}\mu'_s$ (this definition of D is the most widespread, but other definitions exist, for example $D=\frac{1}{3}(\mu'_s+\mu_a)$, which does not change anything if $\mu_a \ll \mu'_s$, which in general defines the scope of validity of the approximation of the diffusion).

The absorption coefficient is $\mu_a=0.1$ cm$^{-1}$.

It is further assumed that the optical properties are the same at the two wavelengths, refractive index n=1.0, which gives a velocity of propagation in the medium $c_n=3.10^8/n$.

This results in an apparent velocity:

$$v_{app} = 2\frac{c}{n}\sqrt{\mu_a D} = 3.4469 \times 10^7 \text{ m}\cdot\text{s}^{-1}.$$

The fluorophore chosen has a lifetime $\tau=1.5$ ns, conventional order of magnitude for fluorophores that are used in optical molecular imaging.

It is assumed that one carries out:
a first measure $(<t>_\infty - \tau) \times v_{app} = 4.7000$ cm, with the source positioned at the surface of the medium at (0.0, 0.0) and a detector positioned at (1.0 cm, 0.0). This signifies that the fluorophore is placed on the semi-ellipse of equation:

$\xi_1$:

$$\sqrt{(x-x_{s1})^2+(y-y_{s1})^2} + \sqrt{(x-x_{d1})^2+(y-y_{d1})^2} =$$

$$v_{app} \times \left(\frac{\langle t \rangle_{mes1}}{\text{measured moment of order }1=m1} - \tau\right) = 4.7$$

a second measure $(<t>_\infty - \tau) \times v_{app} = 5.1000$ cm, with the source positioned at the surface of the medium at (0.5 cm, 0.0) and a detector at (1.5 cm, 0.0). This signifies that the fluorophore is placed on the semi-ellipse of equation $\xi_2$:

$$\sqrt{(x-x_{s2})^2+(y-y_{s2})^2} + \sqrt{(x-x_{d2})^2+(y-y_{d2})^2} =$$

$$v_{app} \times \left(\frac{\langle t \rangle_{mes2}}{\text{measured moment of order }1=m1} - \tau\right) = 5.1$$

Figure 3:
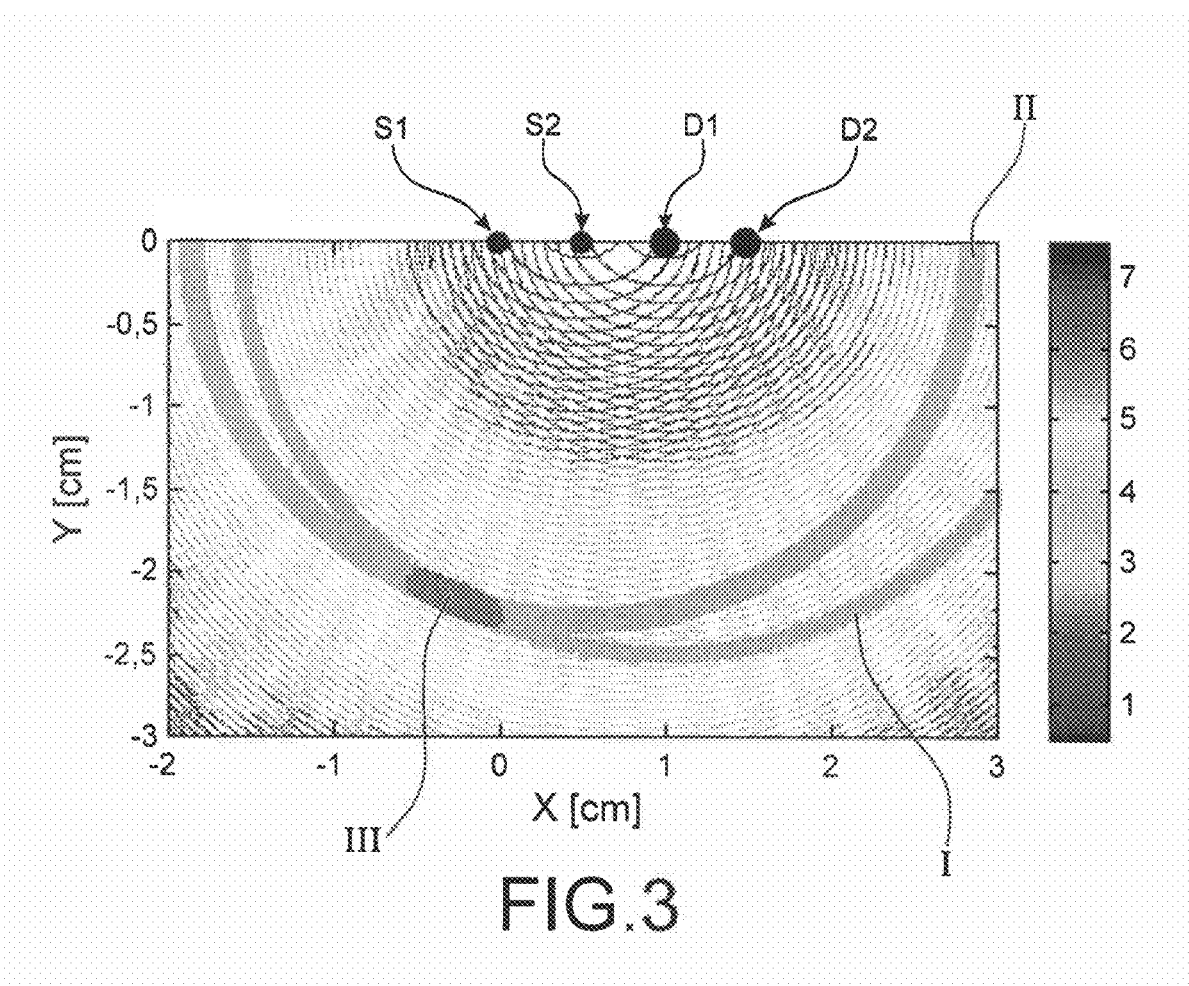
FIG. 3 represents a theoretical configuration, in two dimensions.

FIG. 3 represents the intersection (zone III) of two ellipses I and II thereby defined, this intersection gives the position of the fluorophore. In two dimensions, the method according to the invention thus gives satisfactory results. Examples in 3 dimensions will now be given.

Example II

The experimental set up (FIG. 4A) is substantially that of FIG. 1A with a laser diode 8 of emission wavelength at around 635 nm (H&B laser diode) as excitation source and a photomultiplier 4 coupled to a TCSPC card.

The vessel 21 is filled with a liquid scattering medium 20 composed of water and Acronal® (acrylic resin, BASF) beads, which leads to the following optical parameters:
$\mu a=0.01$ cm$^{-1}$,
$\mu' s=8.7$ cm$^{-1}$ It is considered that the optical properties are identical at the excitation wavelength and at that of emission, on account of the closeness of excitation and diffusion wavelengths, sufficient to consider these coefficients constant over this wavelength range.

The fluorescent medium considered is Cy5 of 10 µMol concentration. The lifetime $\tau$ is 0.96 ns, and the refractive index $n_0$ of the medium is 1.33.

Figure 4A:
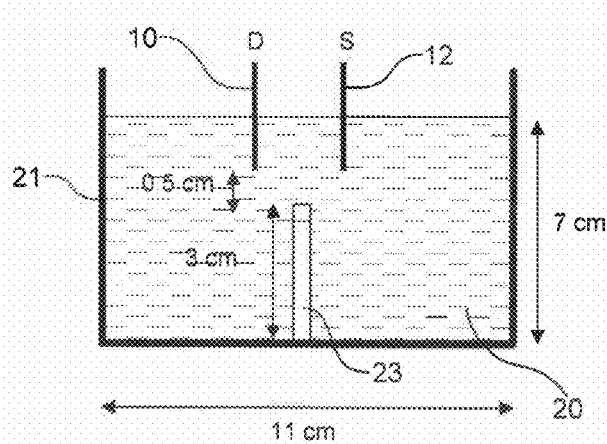
FIGS. 4A-4F represent the experimental device for a measure taken, the positioning of the source and detection points, the measured fluorescence curves, and the calculated position and the real position of a fluorophore.

FIG. 4A represents in a more detailed manner the positioning of the sample in the vessel 21. This is placed in a glass capillary tube 23, of 1 mm internal diameter, over a height of around 2 mm.

Also shown in this figure are the portion of fibres 10 and 12 that are immersed in the examined medium. The end of each fibre is situated at 3.5 cm under the level of the liquid, which is sufficient to assure the condition of infinite medium. The power measured at the outlet of the excitation fibre 10 is 100 µW.

Also represented in this figure are the respective positions of the sample and ends of fibres.

From the modelling point of view, the source not being a spot source, everything takes place as if it became a spot source at a distance of a transport mean free path, i.e. at a distance of 1/µ's (which is indeed the case in the envisaged configuration, since the distance between the ends of fibres and the sample is 0.5 cm, whereas 1/µ's<0.12 cm<0.5 cm).

5 measures are taken, with source and detection positions indicated below.

The 5 positions along Si (i=1, . . . 5) of the source are selected (in fact: the end of the fibre 10; all the coordinates are in cm):

S1: $r_{s1}$=[0.5, 0, −3.5],
S2: $r_{s2}$=[0, 0.25, −3.5],
S3: $r_{s3}$=[1, 0.5, −3.5],
S4: $r_{s4}$=[0.5, 0.5, −3.5];
S5: $r_{s5}$=[0.5, 0.75, −3.5];

And the 5 positions along Di (i=1, . . . 5) of the detector (in fact: the end of the fibre 12; all coordinates also in cm):

D1: $r_{d1}$=[−0.5, 0, −3.5],
D2: $r_{d2}$=[0, −0.25, −3.5],
D3: $r_{d3}$=[0, 0.5, −3.5];
D4: $r_{d4}$=[0.5, 0, −3.5];
D5: $r_{d5}$=[0.5, 0.25, −3.5]

For the position Si of the source, the detector is in position Di.

Figure 4B:
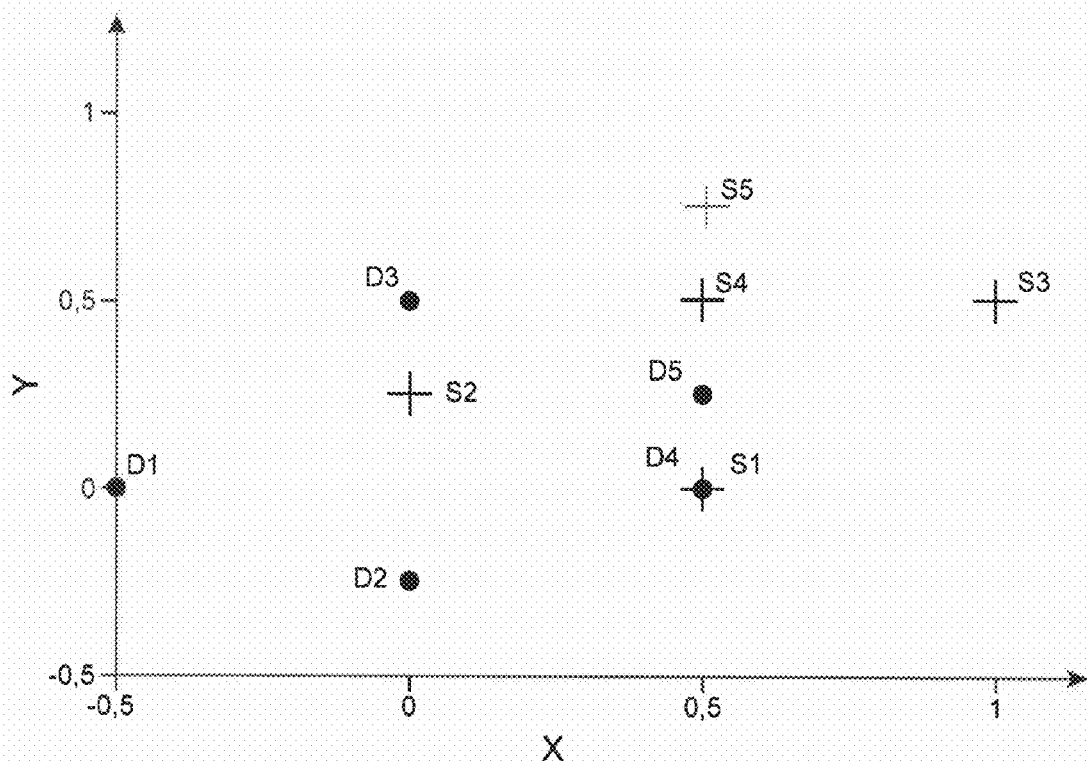

FIG. 4B gives each of the positions Si and Di (i=1, . . . 5) in the plane X, Y (Z is set at −3.5 cm). The distances di calculated between Si and Di are: d1=2.27 cm; d2=2.01 cm; d3=2.73 cm; d4=2.39 cm; d5=2.53 cm.

Figure 4C:
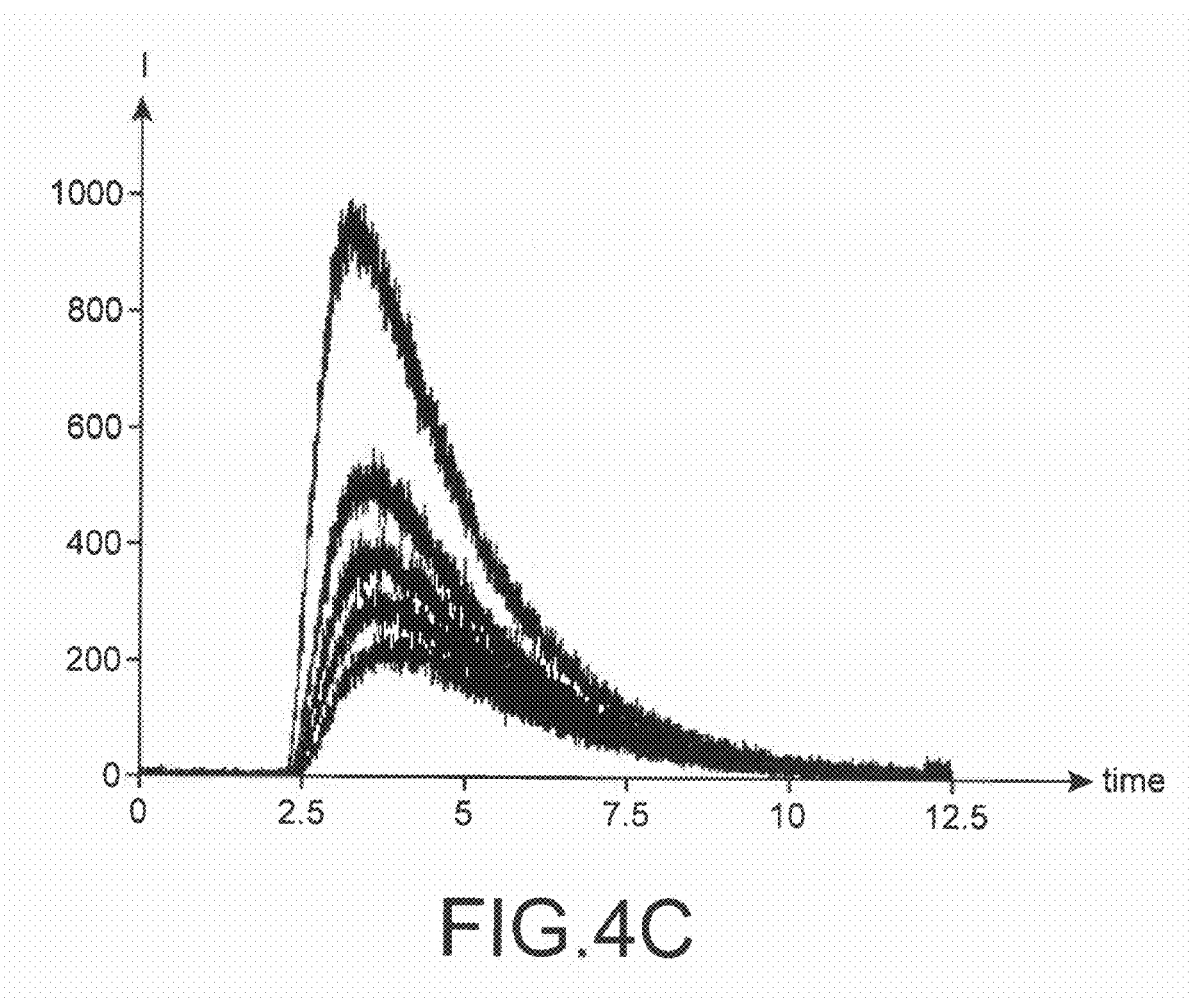

FIG. 4C gives the fluorescence curve obtained for each position pair (Si, Di). The curves have been processed beforehand as explained in A. Laidevant et al., Applied Optics, 45, 19, 4756 (2006).

The measured values of $v_{app}(<t>_{mes1})$ are as follows (it will be recalled that $<t>_{mes1}$ is the measured $1^{st}$ order moment):

For (S1, D1): 2.2700 cm;
For (S2, D2): 2.0059 cm;
For (S3, D3): 2.7284 cm;
For (S4, D4): 2.3931 cm;
For (S5, D5): 2.5258 cm.

Beginning with measures carried out for 3 of the 5 pairs of points ((S1, D1), (S3, D3) and (S4, D4)), three three-dimensional surfaces have been calculated, in fact three ellipsoids, in accordance with the teaching of the invention.

The intersection of these three surfaces has also been calculated.

The 3 surfaces have been elaborated by considering a gridding:

Along x: of 50 points between x=−0.5 cm and x=2 cm;
Along y: of 30 points between y=−0.5 cm and y=1 cm;
Along z: of 50 points between z=−6 cm and z=−3.5 cm.

The fluorophore has been localised in the following position $(x_1, y_1, z_1)$:

−0.041<$x_1$<0.062;
0.12<$y_1$<0.17
−0.91<$z_1$<−3.81.

Figure 4D:
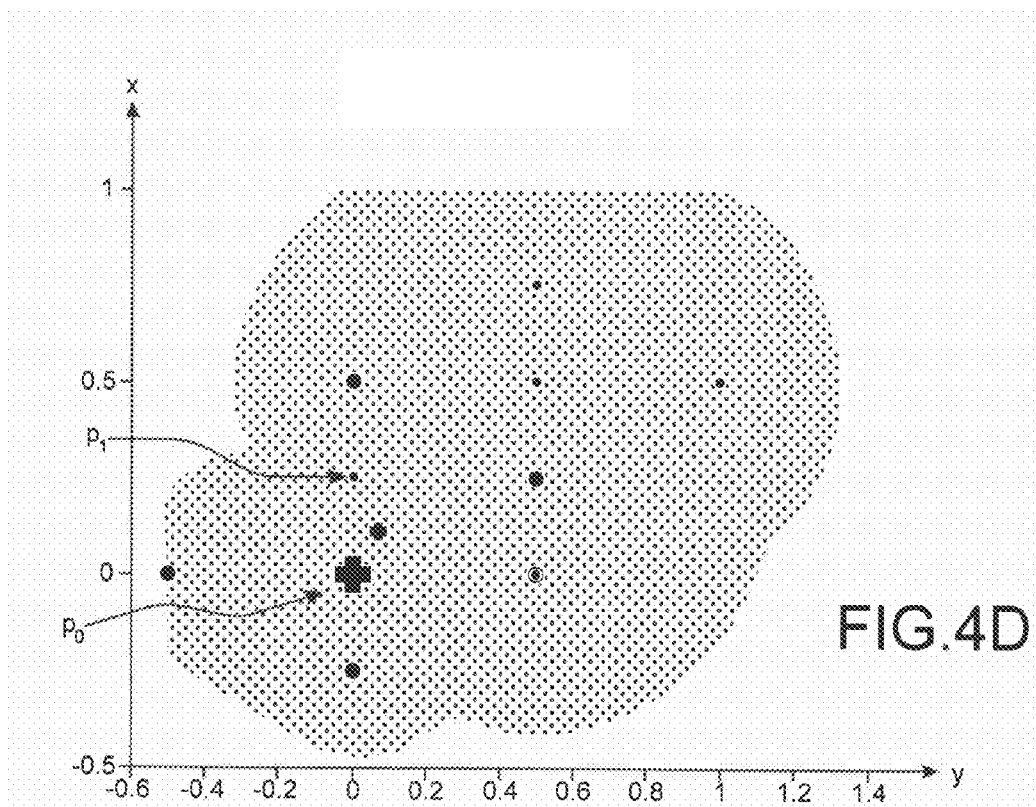
Figure 4E:
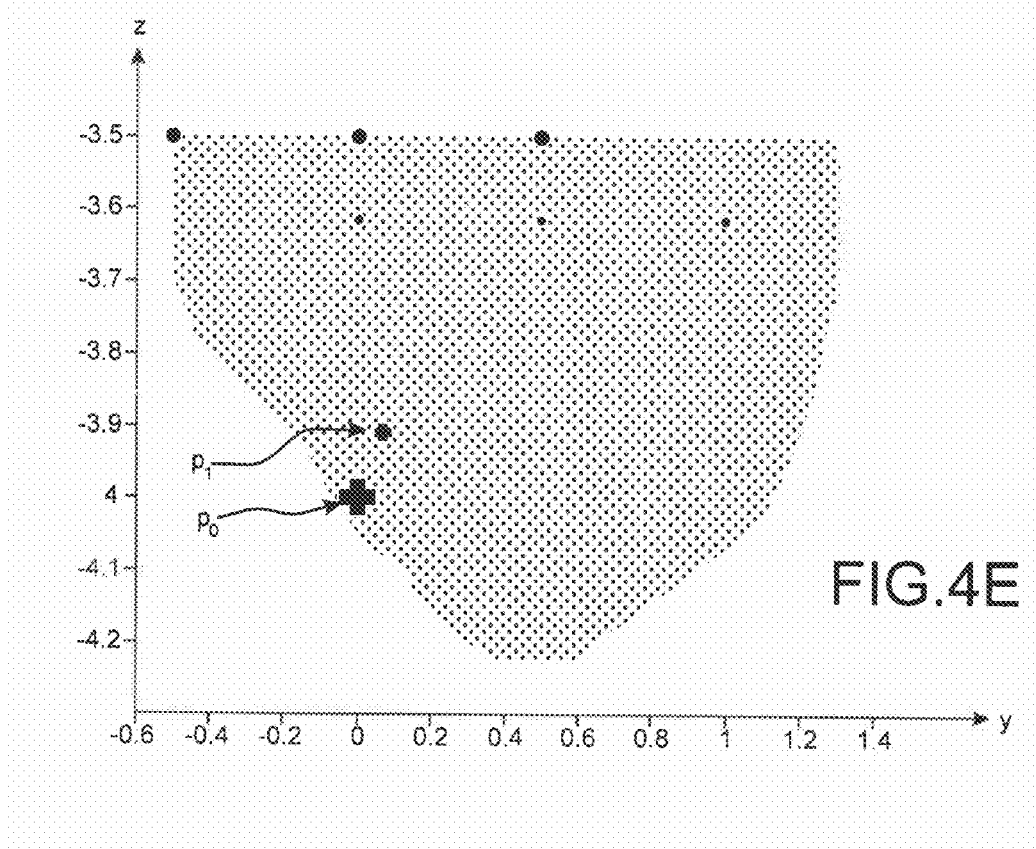
Figure 4F:
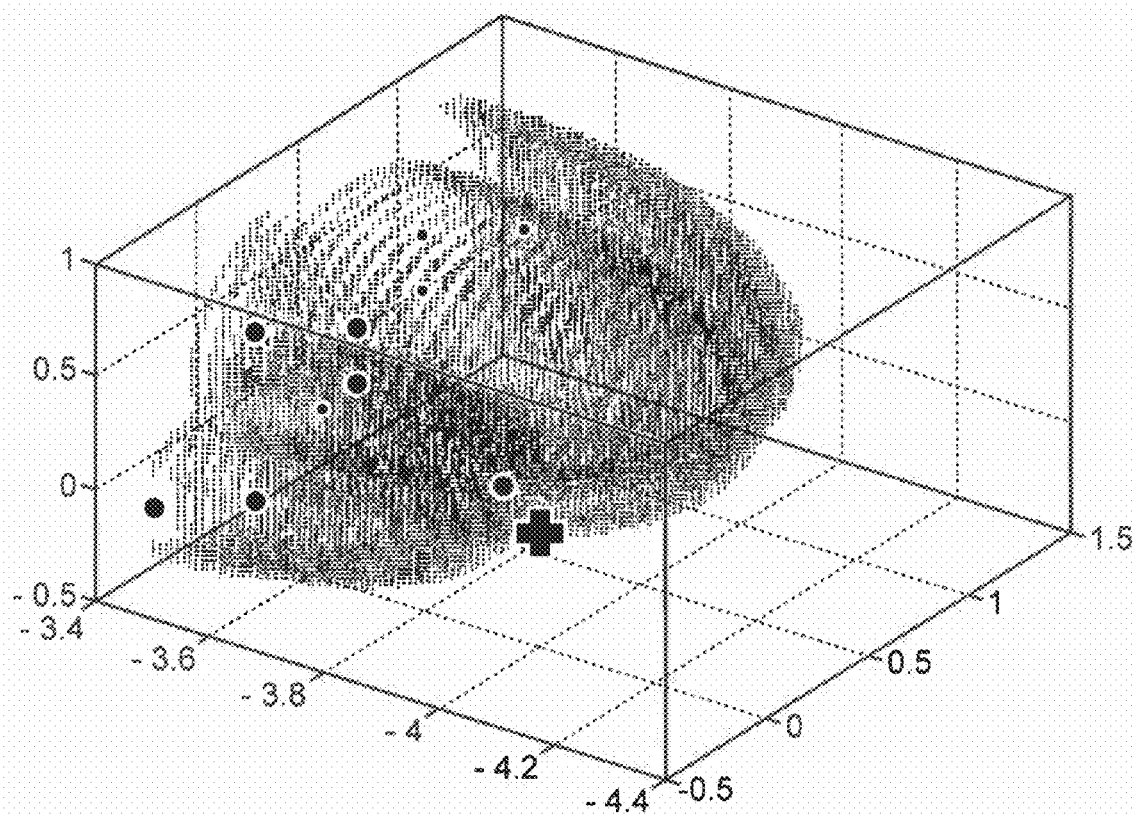

It will be recalled that the real position is (0.0, −4). FIGS. 4D and 4E represent in each of the planes XY and ZY (thus respectively in top view and in side view of the vessel 21) the measured position $p_1$ and the calculated position $P_0$, with a slight shift between these two positions. FIG. 4F represents these two positions in three dimensions, with, also, a slight shift between these two positions. Despite this shift, it is noted that the information obtained by the calculation is entirely satisfactory for a good number of cases, for example for an approximate localisation in an organ of the human body.

The time necessary for these calculations, for the chosen meshing or gridding (with the gridding retained) with "Matlab" software, on a 2.13 GHz Intel Core2 processor, with 1Go of RAM is less than 3 seconds:

calculation time of the distances di for the three pairs (Si, Di) selected: 2.6 s
calculation time of the equations of the 3 ellipsoids ($\xi_1$, $\xi_2$, and $\xi_3$): 0.12 s
calculation time of the determination of the intersection: 0.04 s.

The total calculation time with standard computer equipment is entirely compatible with a measure on or in an organ of the human body, for example during a surgical intervention or in an analysis unit.

The calculation has then been repeated, while taking into account all of the 5 measures: the intersection of 5 surfaces has thus been calculated.

The fluorophore has then been localised in position $(x_2, y_2, z_2)$=(0.06; 0.12; 3.91). This new position is quite close to the preceding one: the localisation performed with only three surfaces is thus sufficient.

Example III

This example is in three dimensions, and in semi-infinite medium.

3 pairs of positions of the source and the detector $(r_s, r_d)$ are considered.

For example, there are the following 3 positions of the source (all the coordinates are in cm):
$r_{s1}$=[0.0, 0, 0], $r_{s2}$=[0.5, 0, 0], $r_{s3}$=[0.75, −1, 0];

And the following 3 positions of the detector (all coordinates also in cm):
$r_{d1}$=[1.0, 0, 0], $r_{d2}$=[1.5, 0, 0], $r_{d3}$=[0.75, 0.5, 0]

Figure 5A:
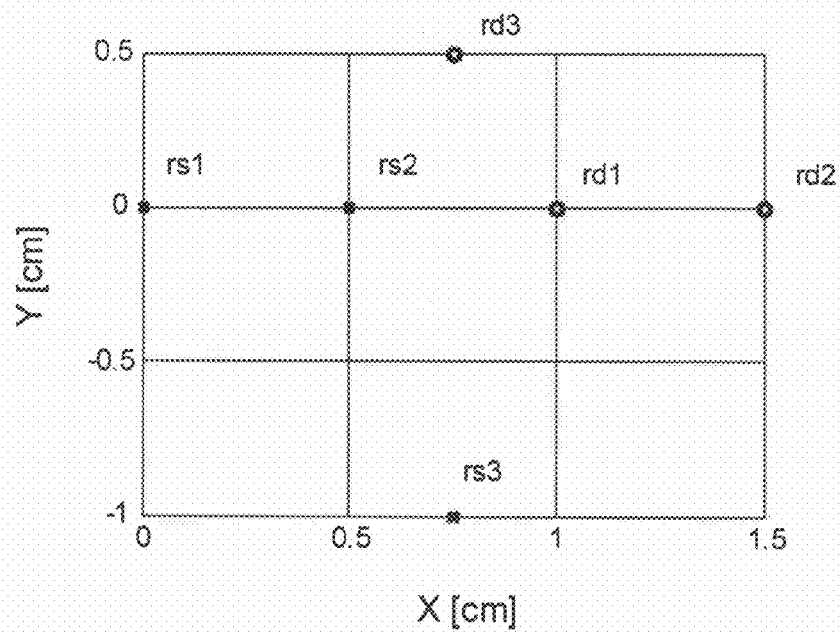
FIG. 5A represents position pairs of a source and a detector, in a plane XY, for the purpose of a measure according to the invention, in semi-infinite configuration.

These 3 pairs are represented in FIG. 5A.

The optical properties are the same as in the preceding example.

It is assumed that the following are carried out:
a first measure $(<t>_\infty - \tau) \times v_{app}$=4.6000 cm, for the position pairs $(r_{s1}, r_{d1})$,
a second measure $(<t>_\infty - \tau) \times v_{app}$=5.6000 cm, for the position pairs $(r_{s2}, r_{d2})$,
a third measure $(<t>_\infty - \tau) \times v_{app}$=4.6000 cm, for the position pairs $(r_{s3}, r_{d3})$.

Then the position of the fluorophore belongs to the intersection of ellipsoids, which have for equations the following:

$$\xi_2: f(|r_{s2+} - r|, |r_{s2-} - r|, k(0)) + f(|r - r_{d2+}|, |r - r_{d2-}|, k(0)) = v_{app} \times \left( \frac{<t>_{mes1}}{\text{measured moment of order } 1=m1} - \tau \right) = 4.6$$

$$\xi_3: f(|r_{s3+} - r|, |r_{s3-} - r|, k(0)) + f(|r - r_{d3+}|, |r - r_{d3-}|, k(0)) = v_{app} \times \left( \frac{<t>_{mes1}}{\text{measured moment of order } 1=m1} - \tau \right) = 5$$

$$\xi_1: f(|r_{s1+} - r|, |r_{s1-} - r|, k(0)) + f(|r - r_{d1+}|, |r - r_{d1-}|, k(0)) = v_{app} \times \left( \frac{<t>_{mes1}}{\text{measured moment of order } 1=m1} - \tau \right) = 4.6$$

Figure 5B:
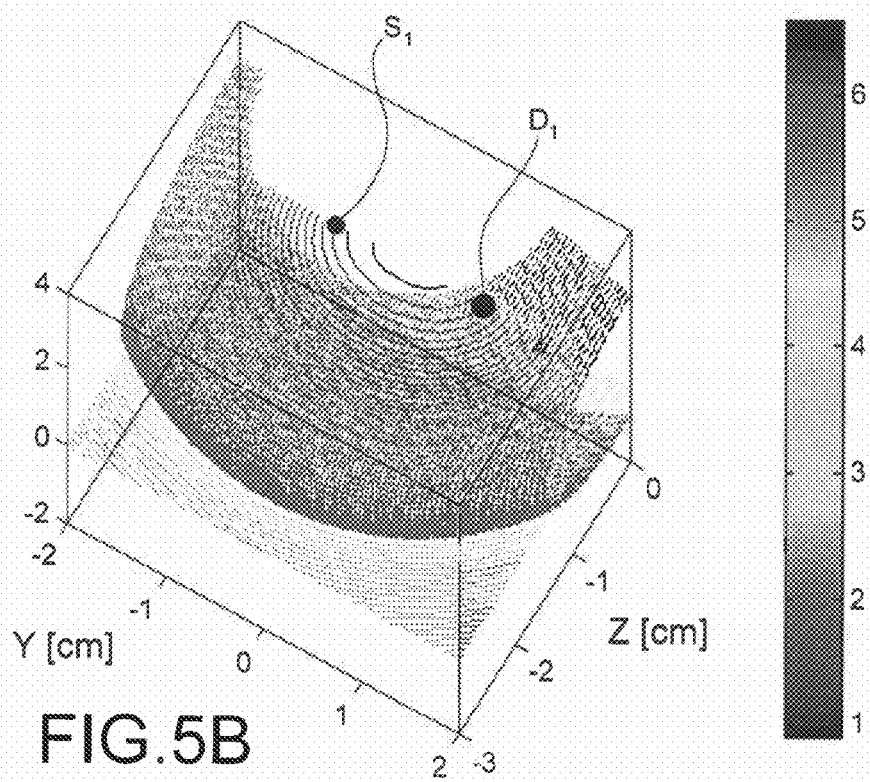
FIGS. 5B-5D represent portions of ellipsoids used within the scope of a measure according to the invention, in semi-infinite configuration, FIGS. 6A-6C each represent a localisation of a fluorophore obtained with a method according to the invention, in semi-infinite configuration.
Figure 5C:
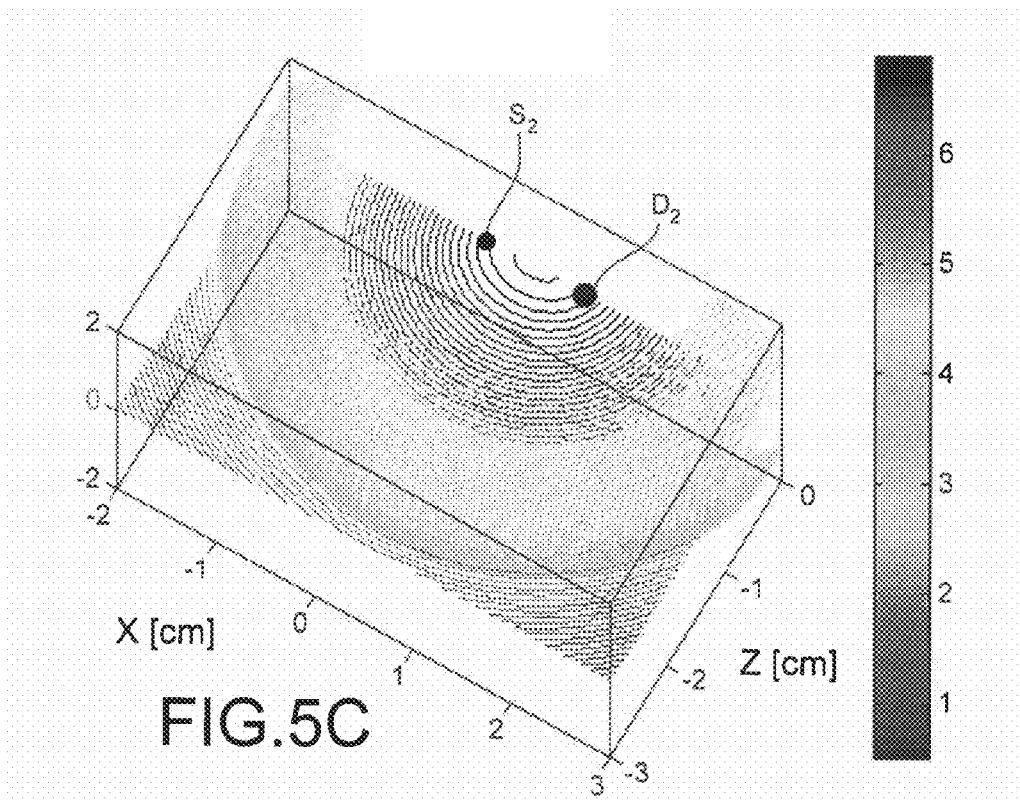
Figure 5D:
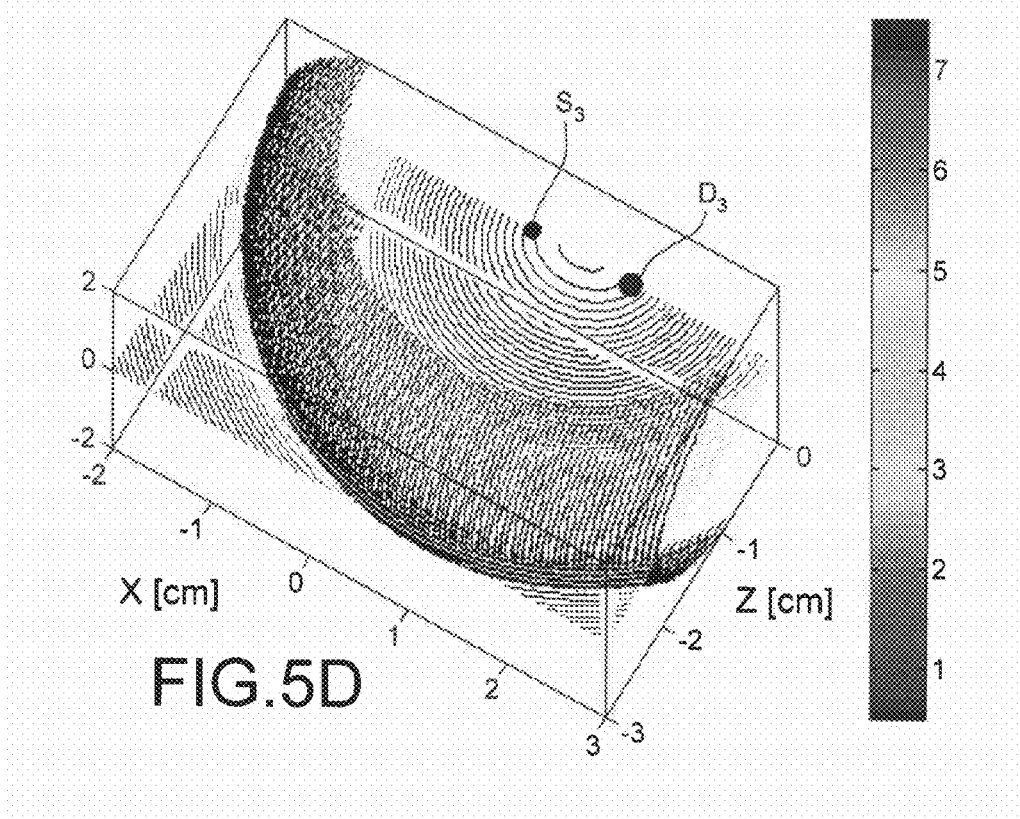

In each of FIGS. 5B, 5C, 5D is represented a part of each of the corresponding ellipsoids.

Figure 6A:
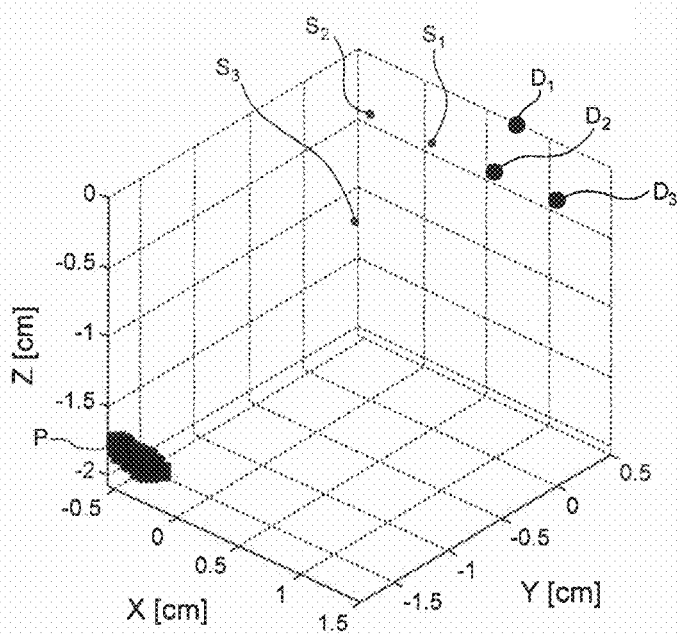

The intersection zone of these 3 ellipsoids is identified by the zone I in FIG. 6A, on which are moreover represented the three positions S1, S2, S3 of the source and the three positions D1, D2, D3 of the detector used for the three measures. The zone P is the localisation zone of the fluorophore.

The figures have been elaborated by considering a meshing or gridding:
Along x: 101 points between x=−2 and x=3;
Along y: 101 points between x=−2 and x=2;
Along z: 101 points between x=−3 and x=0;

The solution of FIG. 6A is an approximate solution, to more or less 10%.

Figure 6B:
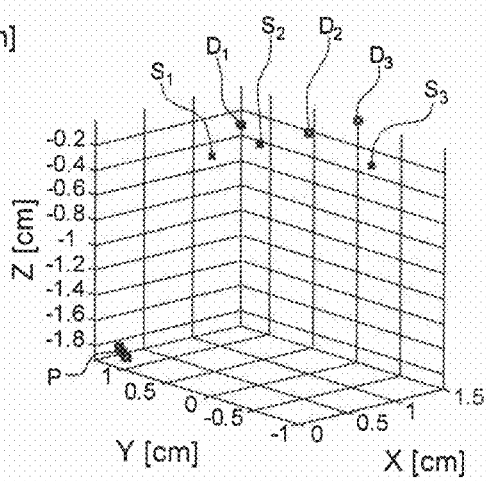
Figure 6C:
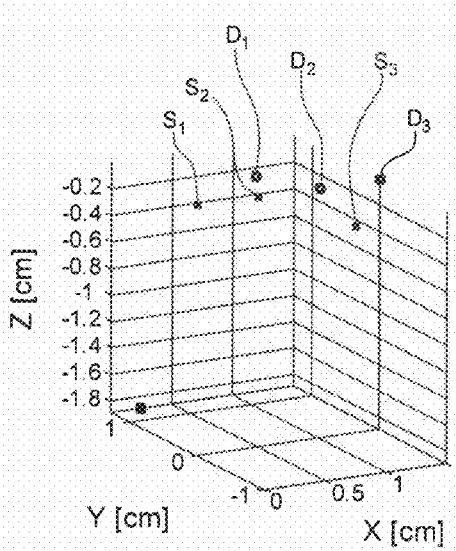

It is possible to impose a greater precision. Thus, in FIGS. 6B and 6C, are represented more precise solutions (zone P):
In FIG. 6B: solution to more or less 2%,
In FIG. 6C: solution to more or less 1.4%.

It will be seen that the increase in precision provides little additional information for an approximate localisation of the fluorophore.

It is worthwhile evaluating the time necessary for these calculations, with "Matlab" software, on a 2.13 GHz Intel Core2, with 1Go of RAM:
for the calculation of the moments for the 3 source-detector pairs at each point of the gridding: 5.6835 s,
for the calculation of the equations of the 3 ellipsoids ($\xi 1$, $\xi 2$, and $\xi 3$): 2.086609 s,
for the calculation of the determination of the intersection: 2.253164 s.

This results in a total time of around 10 s for the chosen meshing or gridding.

This result clearly illustrates the "real time" or rapid character of the method.

Within the scope of a surgical application, a practitioner can carry out an analysis according to the invention even though he/she is in the presence of a patient. A time of 10 s, or even a slightly longer time, is entirely compatible with keeping a patient on an operating table or in an analysis room.

The determination of the position of the fluorophore depends on its lifetime. To dispense with this, differential measures may be considered, as explained in patent application EP 1 884 765.

For example:
With the above configurations of sources-detectors, in semi-infinite medium, one has the following ellipsoids:

$\xi_1$:
$$f(|r_{s1+} - r|, |r_{s1-} - r|, k(0)) + f(|r - r_{d1+}|, |r - r_{d1-}|, k(0)) =$$
$$v_{app} \times \left( \frac{\langle t \rangle_{mes1}}{\text{measured moment of order } 1=m1} - \tau \right) = 4.7$$

$\xi_2$:
$$f(|r_{s2+} - r|, |r_{s2-} - r|, k(0)) + f(|r - r_{d2+}|, |r - r_{d2-}|, k(0)) =$$
$$v_{app} \times \left( \frac{\langle t \rangle_{mes1}}{\text{measured moment of order } 1=m1} - \tau \right) = 5$$

$\xi_3$:
$$f(|r_{s3+} - r|, |r_{s3-} - r|, k(0)) + f(|r - r_{d3+}|, |r - r_{d3-}|, k(0)) =$$
$$v_{app} \times \left( \frac{\langle t \rangle_{mes1}}{\text{measured moment of order } 1=m1} - \tau \right) = 4.6$$

The 3rd corresponds to a measure for which the optical path is the shortest of the three. It is this measure which, as explained in application EP 1 884 765, may be used as reference measurement.

If one considers the quantities $$\xi_1 - \xi_3 = 0.1$$

and $$\xi_2 - \xi_3 = 0.4,$$

Relations independent of the lifetime are obtained.

These quantities no longer define ellipsoids but more complex surfaces.

Figure 7A:
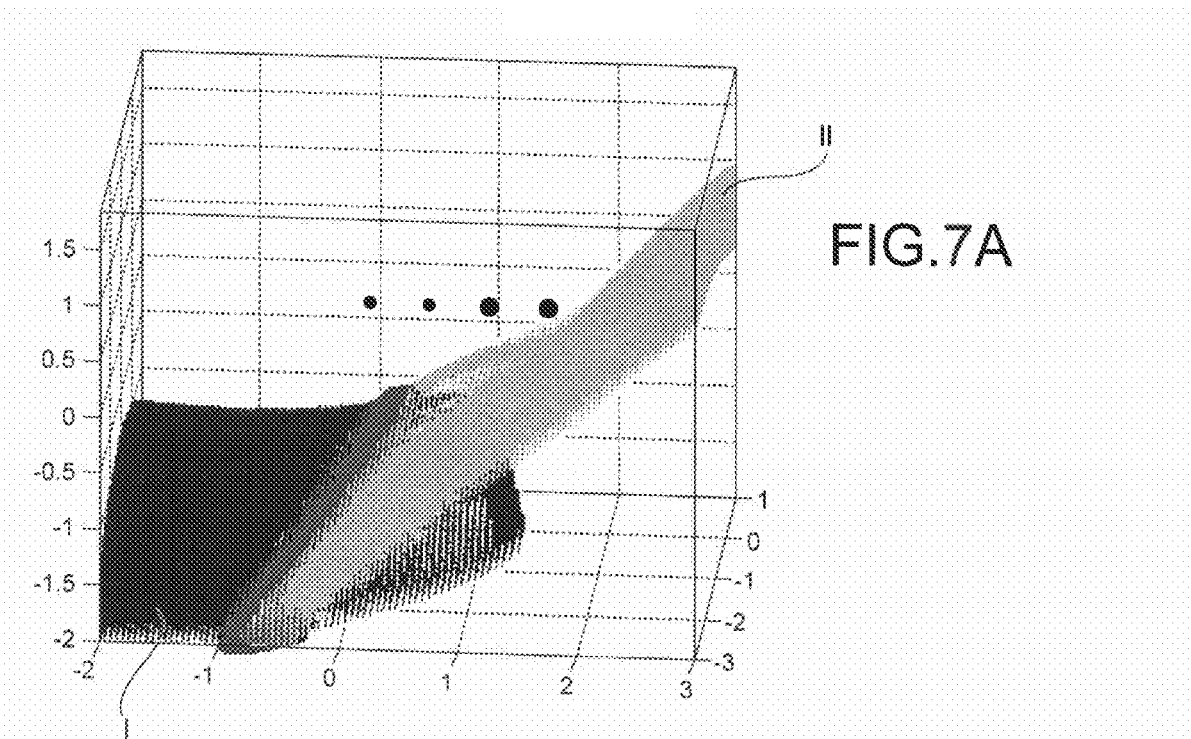
FIGS. 7A-7D represent surfaces implemented within the scope of another embodiment of the invention.
Figure 7B:
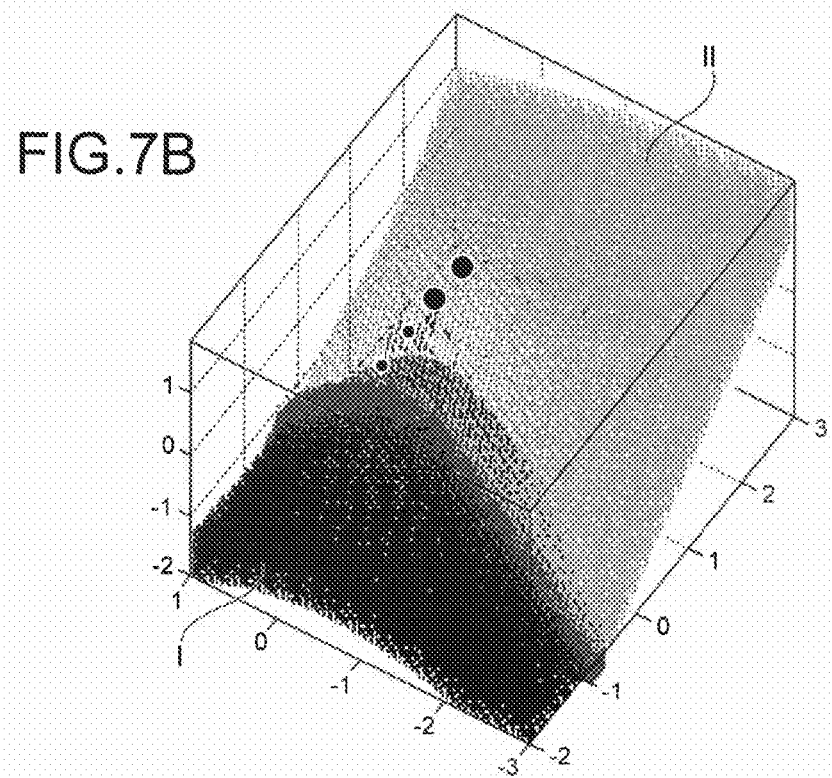

FIGS. 7A and 7B represent, along two different orientations, the intersection between the two 3D surfaces $\xi_1 - \xi_3$ (zone I in these figures) and $\xi_2 - \xi_3$ (zone II in these figures).

In 3D, a third surface is necessary to identify a possible localisation of the fluorophore.

One thus considers a series, not of 3 measures, but of 4 measures.

For example, one has the following 4 positions of the source (all coordinates also in cm):
$r_{s1} = [0.0, 0, 0]$, $r_{s2} = [0.5, 0, 0]$, $r_{s3} = [0.75, -1, 0]$; $r_{s4} = [-0.75; -1.5; 0]$;

And the following 4 positions of the detector (all coordinates also in cm):
$r_{d1} = [1.0, 0, 0]$, $r_{d2} = [1.5, 0, 0]$, $r_{d3} = [0.75, 0.5, 0]$; $r_{d4} = [0.75, 1, 0]$.

One thus obtains, apart from the 3 surfaces $\xi_1$, $\xi_2$, $\xi_3$ already defined, a surface $\xi_4$ (which also defines an ellipsoid):

$\xi_4$:
$$f(|r_{s4+} - r|, |r_{s4-} - r|, k(0)) + f(|r - r_{d4+}|, |r - r_{d4-}|, k(0)) =$$
$$v_{app} \times \left( \frac{\langle t \rangle_{mes1}}{\text{measured moment of order } 1=m1} - \tau \right) = 5.0$$

This surface $\xi_4$ will also be normalised. One thus takes the difference $\xi_4 - \xi_3$ which itself defines a surface, the intersection of which with the surfaces $\xi_1 - \xi_3$ and $\xi_2 - \xi_3$ will make it possible to localise the fluorophore.

Figure 7C:
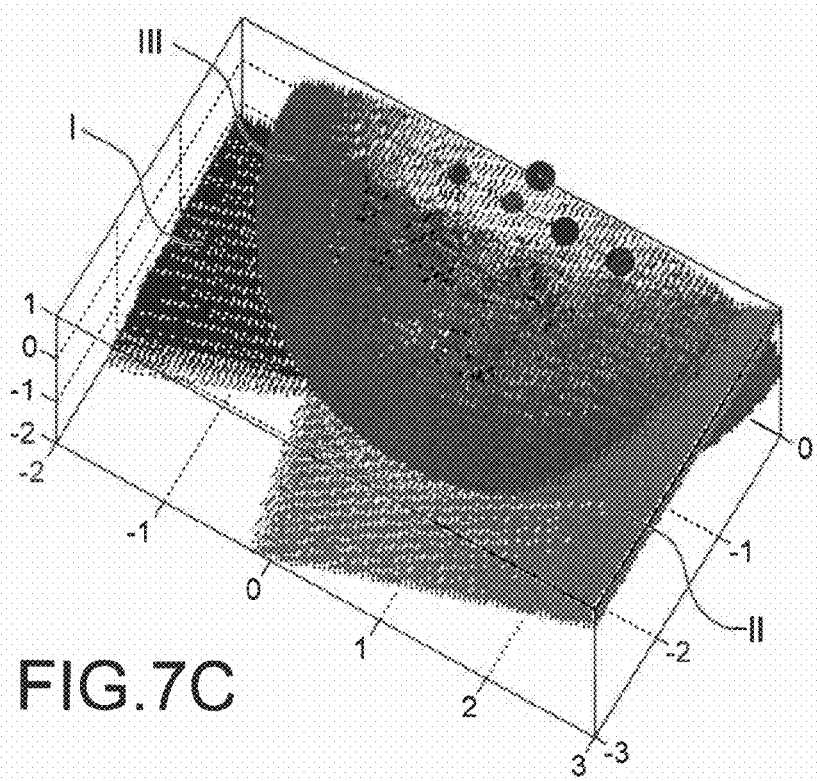
Figure 7D:
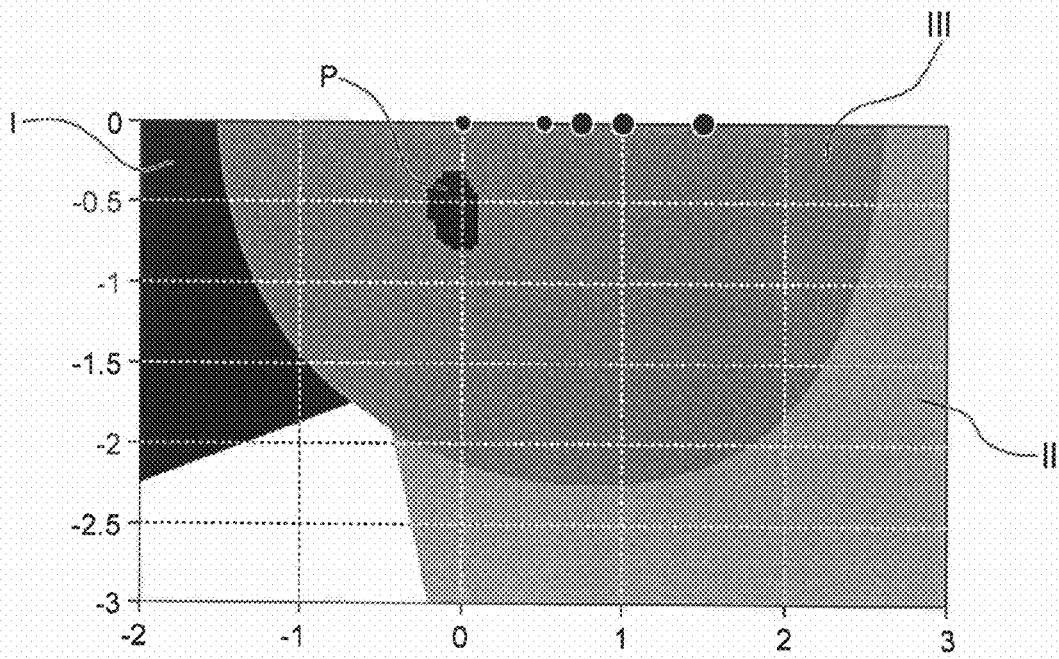

FIG. 7C represents the 3 surfaces $\xi_1 - \xi_3$, (zone I), $\xi_2 - \xi_3$ (zone II) and $\xi_4 - \xi_3$ (zone III), whereas FIG. 7D represents a section of the whole in a plane XZ.

The intersection zone of the 3 surfaces, and thus the localisation zone of the fluorophore is identified by the zone P in this FIG. 7D.

Example IV

This example is in three dimensions, and in "slab" type geometry.

The slab considered is of thickness L=1.5 cm.

3 position pairs of the source and the detector ($r_s$, $r_d$) are considered.

For example, one has the following 3 positions of the source (all the coordinates are in cm):
$r_{s1} = [0.0, 0, 0]$, $r_{s2} = [0.5, 0, 0]$, $r_{s3} = [0.75, -1, 0]$;

And the following 3 positions of the detector (all coordinates also in cm):
$r_{d1} = [1.0, 0, 0]$, $r_{d2} = [1.5, 0, 0]$, $r_{d3} = [0.75, 05, 0]$ As in the preceding examples, one obtains the definition of three ellipsoids, for the three following values of $v_{app}$ ($\langle t \rangle_{mes}$): 1.84; 1.93; 1.81.

Figure 8A:
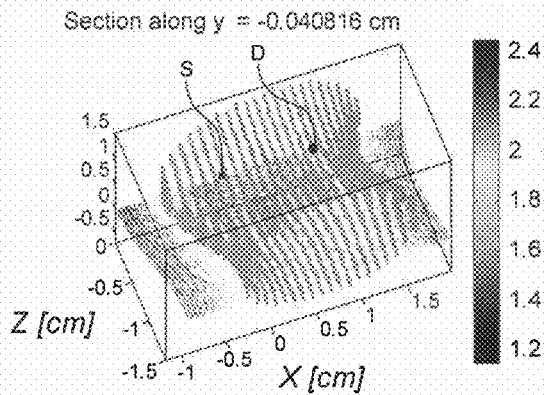
FIGS. 8A-8D represent portions of surfaces used within the scope of a measure according to the invention, in slab configuration.
Figure 8B:
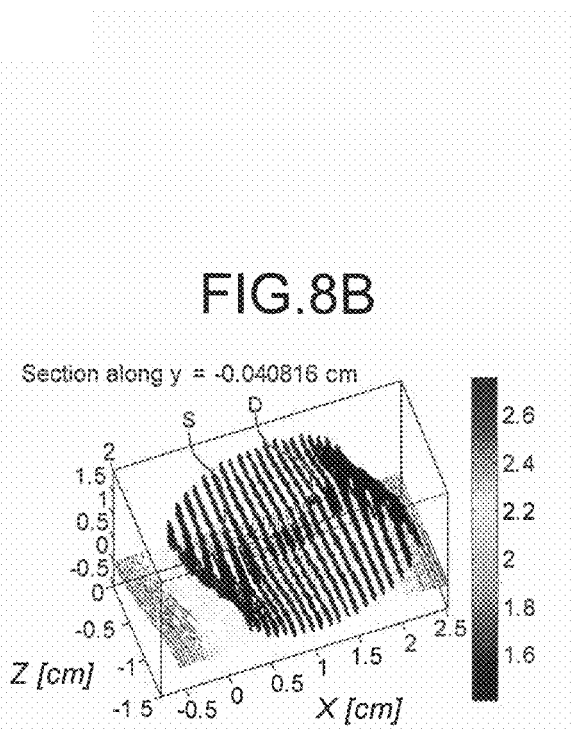
Figure 8C:
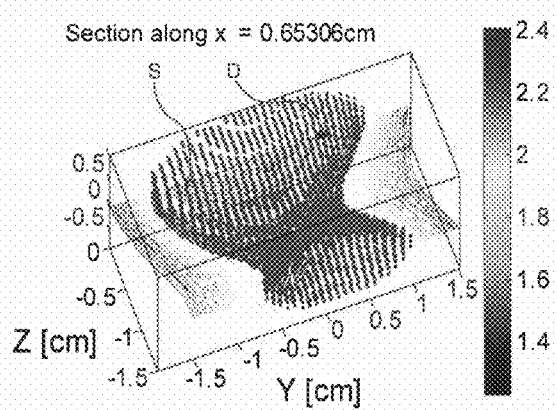

In each of FIGS. 8A, 8B, 8C is represented a part of each of the corresponding ellipsoids.

In these figures, the slab constituting the medium is delimited by the two parallel planes: Z=0 and Z=−1.5 cm.

Figure 8D:
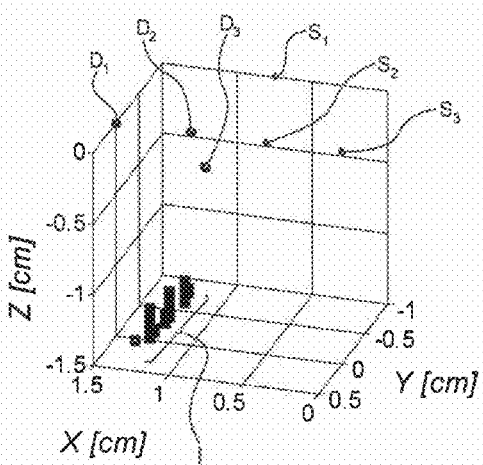

The intersection zone of these 3 ellipsoids is identified by the zone I in FIG. 8D, in which moreover are represented the three positions of the source and the three positions of the detector, used for the three measures.

Figure 9:
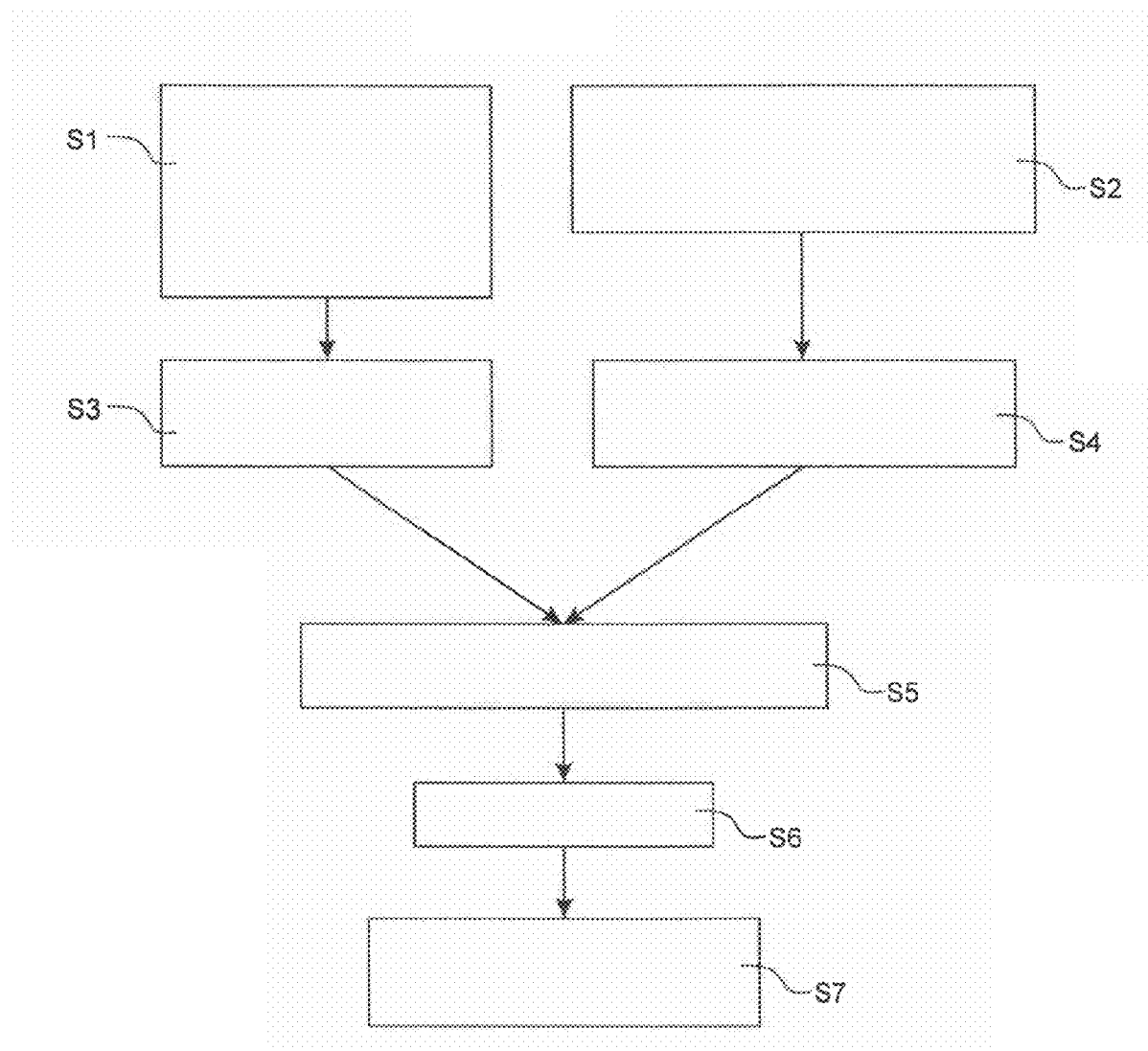
FIG. 9 represents a bock flow diagram of a method according to the invention.

Generally speaking, an example of method according to the invention may be implemented according to the diagram represented in FIG. 9.

The steps of this example, and moreover any other implementation of a method according to the invention, may be preceded by a step—not represented—of injection into the studied medium of at least one fluorophore or absorber intended to fix itself onto a zone of interest. In fact, when a fluorophore is injected, often several of them are injected. A fluorescent zone may moreover be assimilated with an agglomeration of fluorophores. There is generally not only a single fluorescent molecule, but a local concentration of fluorescent molecules. In the same way, when one works in absorption, there is not a single absorbent molecule, but a concentration of absorbent molecules. This concentration may be considered as a spot concentration if the distance separating it from the detector is sufficiently large given its dimensions. Typically, a concentration of radius r is considered as spot, at a given observation distance d, if $d > 10\,r$. Certain absorbers may already be in the medium, for example when it is a zone having an absorption different to its environment.

The emission and detection radiation means are then positioned in relation to the medium. One of the configurations already described may be selected. In particular, an invasive or non-invasive examination.

During a first step S1 of this method, the input data, or parameters, are provided: these are the optical properties of the scattering medium, at the two excitation and emission wavelengths (in certain cases, at these two wavelengths, the optical properties are identical), the geometry of the medium, the positions of the sources and of the detector (in the sense already explained above), and the choice of the meshing or gridding for the calculation of the surfaces. During a second step (S2), the measure files (TPSF) for each source-detector pair are read. A pre-processing of the data may be carried out.

From the data introduced during the first step, an analytical expression of each surface is going to be able to be determined or calculated for each point of the gridding (step S3).

The data stemming from step S2 will enable a calculation of the average times $<t_i>$ for each of the measures carried out (step S4).

The steps S1 and S3 on the one hand, S2 and S34 on the other hand, are represented in FIG. 9 as substantially carried out simultaneously, but this is not necessary, although desirable with a view to carrying out the method as rapidly as possible.

From the calculation data from steps S3 and S4, one searches for the points of the gridding such that $\xi_i = <t_i>$, for any i, to more or less X % (step S5), which signifies $|\xi_i - <t_i>| \leq X/100$. The user may himself set the requisite precision X.

The results (the intersection of the surfaces with each other, and if necessary each of the surfaces individually) may then be visualised (step S6).

If necessary, the calculations may be reiterated by setting a higher (in which case, the precision is decreased) or lower (in which case, the precision is increased) value of X than the preceding value (step S7).

The invention claimed is:

1. A method of localising at least one fluorophore or at least one absorber in a scattering medium, with a pulse radiation source suited to emitting an excitation radiation of said fluorophore or said absorber and a detector suited to measuring a fluorescence signal emitted by said fluorophore or an emission signal emitted by said absorber, comprising:
    a) for at least 3 different pairs of positions of the pulse radiation source and detector, generating at least one excitation by a radiation pulse coming from the pulse radiation source, and performing at least one detection with said detector of an emitted signal corresponding to the fluorescence signal emitted by said fluorophore after said excitation, or to the emission signal emitted by said absorber, said emitted signal representing the number of photons detected, as a function of the time passed t in relation to each radiation pulse,
    b) calculating at least one characteristic parameter of said emitted signal,
    c) for each of said pairs, identifying, based at least on said at least one characteristic parameter of said emitted signal, a surface on which the fluorophore or the absorber is situated, or a volume comprising said surface and in which the fluorophore or the absorber is situated,
    d) estimating a localisation of the fluorophore or the absorber in said scattering medium, by calculating an intersection of the three surfaces, or a volume around said intersection.

2. A method according to claim 1, wherein the medium surrounding the fluorophore or the absorber is of infinite type or semi-infinite type or forms a slab, limited by two parallel surfaces, or is of any shape, its exterior surface being discretised into a series of planes.

3. A method according to claim 1, wherein the medium surrounding the fluorophore or the absorber is of infinite type, the surfaces then having the shape of ellipsoids.

4. A method according to claim 1, said characteristic parameter of said signal comprising, for each position pair, a normalised time moment, of order n ($n \geq 1$), of said emitted signal, or a normalised moment of order n ($n \geq 1$) of a frequency function, deduced from said emitted signal.

5. A method according to claim 4, the frequency function being deduced from a time function by Fourier transform or by Laplace transform or by Mellin transform.

6. A method according to claim 4, wherein the normalised time moment of order n of a time function or the normalised moment of order n is the $1^{st}$ order moment.

7. A method according to claim 1, wherein an excitation is carried out by the pulse radiation source, and a detection by the detector for 4 different pairs of positions of the pulse radiation source and detector.

8. A method according to claim 7, wherein, for the localisation of at least one fluorophore:
    among the four pairs of points are selected the pair of points, known as fourth pair of points, for which the average arrival time of the photons, from the time of emission by the emitter to the time of reception by the receiver, is the shortest, and, for said pair of points, the equation of a surface on which the fluorophore is situated is calculated,
    and, for each of the three other pairs of points, a first equation of a first surface on which the fluorophore is situated is calculated, and a difference is taken between said equation and that associated with the fourth pair, to obtain a second equation of a second surface independent of the lifetime of the fluorophore.

9. A method according to claim 1, wherein, for the localisation of at least one fluorophore, step c) comprises, for each position pair, a calculation of an equation of each surface, independent of the lifetime of the fluorophore.

10. A method according to claim 9, said equation independent of τ resulting from the difference between the average time measured or calculated for each position pair and the average time measured or calculated for a fourth position pair.

11. A method according to claim 10, the fourth position pair being a pair for which the fluorescence signal has a measured average time or a calculated average time less than that of the 3 position pairs.

12. A method according to claim 1, further comprising a visual or graphic representation of the position or the distribution of the fluorophore or fluorophores or the absorber.

13. A method according to claim 1, the emitted signals being detected by TCSPC technique or by camera.

14. A method according to claim 1, the pulse radiation source and the detector comprising an end of an optic fibre.

15. A method according to claim 1, the detector comprising an end of an optic fibre, wherein said optic fiber samples a part of an emitted light.

16. A method according to claim 1, wherein said characteristic parameter of said signal comprises a moment of said emitted signal.

17. A device for the localisation of at least one fluorophore or at least one absorber in a scattering medium, comprising:
- a radiation source suited to emitting pulses of excitation radiation,
- a detector suited to measuring an emitted signal corresponding to a fluorescence signal emitted by said fluorophore or an emission signal emitted by said absorber, said emitted signal representing the number of photons detected, as a function of the time passed t in relation to each pulse of excitation radiation,
- a processor configured to:
  a) for each pair of points among at least 3 different pairs of positions of the radiation source and the detector, calculate at least one characteristic parameter of said emitted signal, after an excitation carried out by a radiation coming from the radiation source, and a detection by the detector of signals emitted by the fluorophore or the absorber after said excitation, and, based at least on said at least one characteristic parameter, calculate a surface on which the fluorophore or the absorber is situated, or a volume comprising said surface and in which the fluorophore or the absorber is situated,
  b) estimate a localisation of the fluorophore or the absorber in said scattering medium, by calculation of an intersection of the three surfaces or of a volume around said intersection.

18. A device according to claim 17, the medium surrounding the fluorophore or the absorber being of infinite type or semi-infinite type or of slab shape, limited by two parallel surfaces, or of any shape, its exterior surface being broken down into a series of planes.

19. A device according to claim 17, wherein said processor is configured to calculate, for each position pair, a normalised time moment, of order n (n≧1), of a time function, or a normalised moment of order n (n≧1) of a frequency function, deduced from said fluorescence or emission signal.

20. A device according to claim 19, the frequency function being deduced from said emitted signal by Fourier transform or by Laplace transform or by Mellin transform.

21. A device according to claim 17, wherein, for the localisation of at least one fluorophore, for each position pair, the processor being configured to calculate an equation of a surface, independent of the lifetime of the fluorophore.

22. A device according to claim 21, wherein the processor is configured to calculate an equation of a surface, independent of the lifetime, by difference between the average time measured or calculated for each position pair and the average time measured or calculated for a fourth position pair.

23. A device according to claim 21, the fourth position pair being a pair for which the fluorescence signal has an average measured time or an average calculated time less than that of the 3 position pairs.

24. A device according to claim 17, said detector comprising TCSPC type means or camera type means.

25. A device according to claim 17, further comprising means of visual or graphic representation of the localisation of the fluorophore or the absorber.

26. A device according to claim 17, wherein said characteristic parameter of said signal comprises a moment of said emitted signal.

27. A device according to claim 17, the pulse radiation source and the detector each comprising an end of an optic fibre.

28. A device according to claim 17, the detector comprising an end of an optic fibre, said optic fibre being configured to sample at least a part of the emission or fluorescence signal.

* * * * *